(12) United States Patent
Kainosho et al.

(10) Patent No.: US 7,022,310 B2
(45) Date of Patent: Apr. 4, 2006

(54) STABLE ISOTOPE-LABELED AMINO ACID AND METHOD FOR INCORPORATING SAME INTO TARGET PROTEIN

(75) Inventors: Masatsune Kainosho, Tokyo (JP); Tsutomu Terauchi, Hachioji (JP)

(73) Assignee: Agency of Industrial Science and Technology, (JP)

( * ) Notice: Subject to any disclaimer, the term of this patent is extended or adjusted under 35 U.S.C. 154(b) by 0 days.

(21) Appl. No.: 10/872,163

(22) Filed: Jun. 18, 2004

(65) Prior Publication Data

US 2005/0084452 A1    Apr. 21, 2005

Related U.S. Application Data

(63) Continuation of application No. PCT/JP02/13303, filed on Dec. 19, 2002.

(30) Foreign Application Priority Data

Dec. 19, 2001  (JP) .............................. 2001-386823
Jan. 30, 2002  (JP) .............................. 2001-022446

(51) Int. Cl.
 A61B 5/055   (2006.01)
 C12P 13/04   (2006.01)
 C12P 9/00    (2006.01)
 C07K 1/00    (2006.01)

(52) U.S. Cl. .................... 424/9.34; 435/106; 435/131; 530/350

(58) Field of Classification Search ................ 530/333, 530/350; 424/1.11, 9.34; 435/71.3, 106, 435/131
See application file for complete search history.

(56) References Cited

FOREIGN PATENT DOCUMENTS

| EP | 0 299 425 A1 | 1/1989 |
|----|--------------|--------|
| JP | 02208579 A   | 8/1990 |
| JP | 05236986 A   | 9/1993 |

OTHER PUBLICATIONS

LeMaster, D. 1994. Isotope Labeling in Solution Protein Assignment and Structural Analysis. Progress in NMR Spectroscopy. 26: 400.*
Venters, R.A., et al. 1995. High-level 2H/13C/15N labeling of proteins for NMR studies. J. Biomol. NMR 5: 339-344.*

(Continued)

*Primary Examiner*—Maryam Monshipouri
*Assistant Examiner*—Marsha Tsay
(74) *Attorney, Agent, or Firm*—Hoffmann & Baron, LLP

(57) ABSTRACT

The present invention provides a stable isotope-labeled amino acid which is at least one of amino acids constituting a protein and which has at least one of the following labeling patterns:

(a) hydrogen atoms except at least one hydrogen atom in one or more methylene groups are deuterated,
(b) hydrogen atoms in one of prochiral gem-methyl groups are completely deuterated,
(c) hydrogen atoms in prochiral methyl groups are partially deuterated, and
(d) all hydrogen atoms except one of them in methyl group are deuterated and hydrogen atoms in the aromatic ring are partially deuterated. With the stable isotope-labeled amino acid, the deuteration of protein can be attained without damaging the NMR sensitivity of remaining hydrogen nucleus and, in addition, the rapid, accurate analysis of NMR spectrum of a high-molecular protein which is beyond the limitation in the prior art and the determination of the stereo-structure can be performed at the same time.

21 Claims, 13 Drawing Sheets

OTHER PUBLICATIONS

Kainosho, M. 1997. Isotope labelling of macromolecules for structural determinations. Nature Structural Biology. NMR suppl. 858-861.*

Sattler, M., et al. 1996. Use of deuterium labeling in NMR: overcoming a sizeable problem. Structure. 4:1245-1249.*

Y. J. Topper, et al., "Note On The Synthesis Of Succinic Acid Labeled In The Carboxyl Position With Radioactive Carbon", J. Biol. Chem. 177, 1949, p303-304.

Tohru Oishi, et al., "Highly Enantioselective Dihydroxylation of Trans-Disubstituted and Monosubstituted Olefins", J. Org. Chem. 1989, 54, pp. 5834-5835.

Stephen Hanessian, et al., "Asymmetric Dihydroxylation of Olefins with a Simple Chiral Ligand", J. Org. Chem. 1993, 58, pp. 1991-1993.

Kiyoshi Tomioka, et al., "Enantioface Differentiation in Cis Dihydroxylation of C—C Double Bonds by Osmium Tetroxide with Use of a Chiral Diamine with $D_2$ Symmetry", J. Am. Chem. Soc. 1987. 109, pp. 6213-6215.

Masahiro Hirama, et al., "Asymmetric Dihydroxylation of Alkenese with Osmium Tetroxide: Chiral N, N'-Dialkyl-2, 2'-bipyrrolidine Complex", J. Chem. Soc., Chem. Commun., 1989, pp 665-666.

Gianfranco Cainelli, et al., "Catalytic Hydroxylation of Olefins by Polymer-Bound Osmium Tetroxide", Communications, Jan. 1989, pp. 45-47.

Dario Pini, et al., "Heterogeneous Catalytic Asymmetric Dihydroxylation of Olefins with the $OsO_4$/(9-O-Acylquinine-co-Acrylonitrile) System", Tetrahedron Letters, vol. 32, No. 38, p. 5175-5178, 1991.

Maritherese Tokles, et al., "Asymmetric Oxidation of Olefins to Vicinal Diols with Osmium Tetroxide", Tetrahedron Letters, vol. 27, No. 34, pp. 3951-3954, 1986.

Makoto Nakajima, et al., "Highly Enantioselective Dihydroxylation of Olefins by Osmium Tetroxide with Chiral Diamines", Tetrahedron letters, vol. 49, No. 47, pp. 10973-10806, 1993.

Easton, Christopher J. et al., "Synthesis of Each Stereoisomer of [3-$^2H_1$] . . . " J. Chem. Soc. Perkin Trans. I (1994), pp. 3545-3548.

Erlenmeyer, H. et al., Helv. Chim. Acta, 22, p. 701-706, 1939.

Gani, David et al., Synthesis of a Monocyclic β-Lactam Stereospecifically Labelled at C-4, J. Chem. Soc. Perkin Trans. I 1983, pp. 2811-2814.

Hoshino, Tsutomu et al., "Biosynthesis of Violacein: Origins of Hydrogen, Nitrogen . . . ", Agric. Biol. Chem., 51 (10), 2733-2741, 1987.

Jorgensen, E.C. et al., "Small Scale Preparation of Carbon-14 Labeled Succinic, Malic, Fumaric and Tartaric Acids", The Radiation Laboratory and Department of Chemistry, University of California, Berkeley, pp. 2418-2419 (1951).

Kobayashi, J. et al., "Nuclear Magnetic Resonance Study of Side-Chain Conformation of Tyrosyl Residue in [Met$^5$]-Enkephalin", Biochimica et Biophysica Acta, 621 (1980) 190-203.

Mahon, Marrita, et al., "The pyridoxal-5'-phosphate-dependent catalytic antibody 15A9: its efficiency and stereospecificity in catalyzing the exchange . . . ", FEBS Letters 427 (1998) 74-78.

Mocek, Ursula et al., "Biosynthesis of the Modified Peptide Antibiotic Thiostrepton in *Streptomyces azureus* and *Streptomyces laurentii*", J. AM. Chem. Soc. 1993, 115, 7992-8001.

Moldes Milagros et al., "$^1H$-$^2H$ Exchange in the Perfused Rat Liver Metabolizing . . . ", NMR IN BIOMEDICINE, vol. 7, 249-262 (1994).

Nystrom, Robert F. et al., J. Am. Chem. Soc., vol. 74, p. 3434, 1952.

Oba, Makoto et al., "Synthesis of 13C/D Doubly Labeled ι-Leucines: Probes for Conformational Analysis of the Leucine Side-chain", J. Org. Chem. 2001, 66, 5919-5922.

Oba Makoto et al., "Asymmetric synthesis of ι-proline regio- and steroselectively labeled with deuterium", Tetrahedron Asymmetry 10 (1999) 937-945.

Oba, Makoto et al., "Synthesis of [3,4-$D_2$]Lysine Using Deuterated Pyroglutamate Derivative As A Chiral Template", Jpn J Deuterium Sci, 1999, 8(1):11-15, p. 11-15.

Oba, Makoto et al., "Stereoselective Synthesis of Deuterium-Labeled Amino Acids Using Diketopiperazine or Proline Derivatives as a Chiral Template", J Deuterium Sci, (1996), 5(1):35-39.

Oba, Makoto et al., "Synthesis of L-*threo*- and L-*erythro*- . . . ", J. Chem. Soc. Perkin Trans. 1(1995), p. 1603-1609.

Prabhakaran, P.C., "Biosynthesis of Blasticidin S from . . . ", J. Am. Chem. Soc. (1988), 110, pp. 5785-5791.

Son, Jong-Keun et al., "Stereochemical Mechanism of Iodoacetic Acid Mediated Decomposition of ι-Methionine to ι-Homoserine Lactone", J. Am. Chem. Soc. (1989), 111, 1363-1367.

Walker, Joel R. et al, "Improved synthesis of (R)-glycine-d-$^{15}N$", Tetrahedron 57 (2001) 6695-6701.

Japanese Article (1991), pp. 204-206.

PCT International Search Report.

PCT International Preliminary Examination Report.

PCT Written Opinion.

* cited by examiner $^1H$-$^{13}C$ HSQC spectrum of EPPlb protein (18.2 kDa) containing SAD-glycine incorporated thereinto HCCT TOCSY spectrum of EPPIb protein (18.2 kDa) containing SAD-lysine incorporated thereinto (a) EPPIb protein containing SAD-lysine (18) incorporated thereinto
(b) EPPIb protein containing [ul-$^{13}C_2$; $^{15}N$] lysine incorporated thereinto HCCT TOCSY spectrum of EPPIb protein (18.2 kDa) containing SAD-glutamine incorporated thereinto (a) EPPIb protein containing SAD-glutamine (18) incorporated thereinto
(b) EPPIb protein containing [ul-$^{13}C_2$; $^{15}N$] glutamine incorporated thereinto (a) EPPIb protein containing SAD/PDM-leucine (33) incorporated thereinto
(b) EPPIb protein containing [ul-$^{13}$C; $^{15}$N]-leucine incorporated thereinto $^1H$-$^{13}C$ HSQC spectrum of EPPIb protein (18.2 kDa) containing SAD/PDM-leucine incorporated thereinto in $^1H$-$^{13}C$ γ region (a) EPPIb protein containing SAD/PDM-leucine (33) incorporated thereinto
(b) EPPIb protein containing [ul-$^{13}C$; $^{15}N$]-leucine incorporated thereinto (a) EPPIb protein containing SAD/PDM-methionine (41) incorporated thereinto
(b) EPPIb protein containing [ul-$^{13}$C; $^{15}$N]-methionine incorporated thereinto $^1H$-$^{13}C$ HSQC spectra in $^1H$-$^{13}C$ β region of EPPlb protein (18.2 kDa) containing an aromatic amino acid SSD-labeled at the β - position (a) Uniform $^{13}C$, $^{15}N$ label by an ordinary method
(b) Amino acid selective label by an ordinary method
(c) Aromatic amino acid in which pro-S proton is deuterated
(d) Aromatic amino acid in which pro-R proton is deuterated Slice data of H 92 signals (a) Uniform $^{13}C$, $^{15}N$ label by an ordinary method
(b) Amino acid selective label by an ordinary method
(c) Histidine residue in which pro-S proton is deuterated
(d) Histidine residue in which pro-R proton is deuterated

FIG. 10a

FIG. 10b

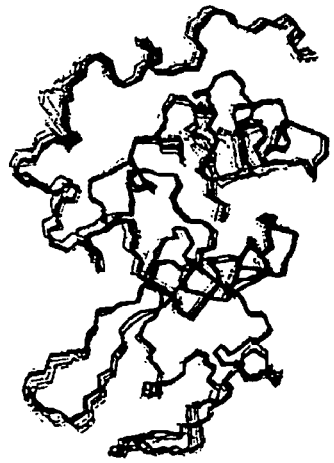

FIG. 10c

FIG. 10d

Simulation of the calculation of structure of lysozyme
(a) Structure obtained by the X-ray analysis of crystal structure
(b) NOE information of all protons
Structure obtained by the main chain dihedral angle information by TALOS and NH-dipole
(c) NOE information of remaining protons after SAD/PDM labeling
Structure obtained by the main chain dihedral_angle information by TALOS and NH-dipole
(d) NOE (CH3, ring, & HN) of only CH3, ring & HN
Structure obtained by the main chain dihedral angle information by TALOS and NH-dipole

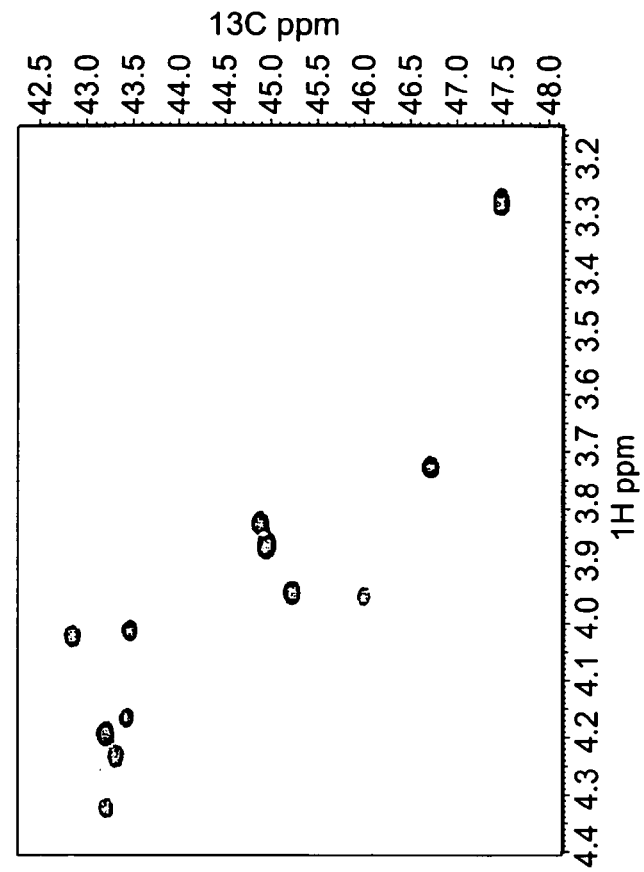
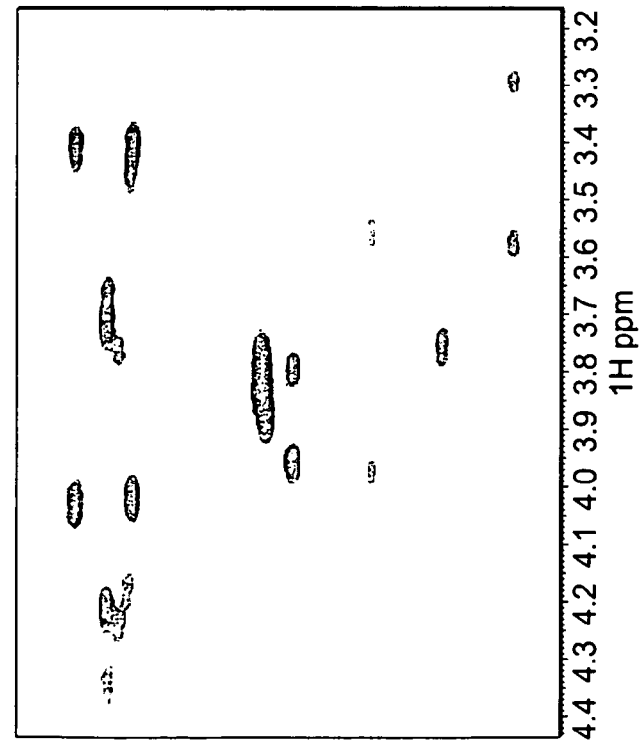
FIG. 12

STABLE ISOTOPE-LABELED AMINO ACID AND METHOD FOR INCORPORATING SAME INTO TARGET PROTEIN

CROSS-REFERENCE TO RELATED APPLICATIONS:

This application is a continuation application of PCT Application No. PCT/JP02/13303, filed on Dec. 19, 2002, which claims priority to Japanese Patent Application No. 2001-386823 filed on Dec. 19, 2001 and Japanese Patent Application No. 2002-22447 filed on Jan. 30, 2002, each of which is incorporated herein by reference.

BACKGROUND OF THE INVENTION

The present invention relates to a stable isotope-labeled amino acid and method for incorporating the same into target protein, and NMR method for the structural analysis of protein. The present invention also relates to a method for producing regio-selectively stable isotope-labeled fumaric acid and tartaric acid. In particular, the present invention relates to a method for efficiently producing symmetric and asymmetric stable isotope-labeled fumaric acid and also a method for producing stable isotope-labeled tartaric acid with a high optical purity.

In the determination of the protein structure by NMR, a sample uniformly labeled with stable isotopes such as $^{13}$C/$^{15}$N has so far been used. However, this technique sharply becomes difficult when the molecular weight of the protein exceeds 20,000. There were proposed methods for solving this problem such as a method wherein about 50 to 80% of hydrogen in the protein is replaced at random with deuterium ($^2$H) in addition to the labeling with $^{13}$C/$^{15}$N to utilize NMR signals of the nucleus of remaining hydrogen ($^1$H) and a method wherein all the hydrogen atoms except those in methyl group and aromatic ring in the amino acid residue are replaced with deuterium. However, the subject and the utility of those conventional methods are limited because these techniques sacrificed of the accuracy of structural information to determine the structure of high-molecular weight proteins.

[1-$^{13}$C, 2,3-$^2$H$_2$]phenylalanine, [$^2$H$_2$]serine and [$^2$H$_2$]alanine are described in a paragraph of Analysis of higher-order structure of protein by main chain carbonyl $^{13}$C-NMR of Protein III Higher-order structure in "*Shin Seikagaku Jikken Koza* (Lectures on New Biochemistry Experiments)" I published by Tokyo Kagaku Dojin on Nov. 15, 1990. However, this technique is employed for the determination of dihedral angle $\chi$ of amino acids by a specific multi-labeling method. It has not yet been tried that not only the labeled amino acids but also other amino acids are labeled and these amino acids are incorporated into a target protein to analyze the stereostructure thereof.

On the other hand, in the analysis of biological organic compounds such as nucleic acids and protein by NMR or mass spectra, fumaric acid and tartaric acid labeled with stable isotopes such as $^{13}$C and $^2$H are widely used. Recently, the following technique for analyzing the structure of protein is employed: isotope-labeled amino acids are derived from isotope-labeled fumaric acid and tartaric acid and the structure of protein is analyzed by using those amino acids by NMR. Under those circumstances, the demand of stable isotope-labeled fumaric acid and also isotope-labeled tartaric acid is expected to increase.

However, in fact, the stable isotope-labeled fumaric acid is quite expensive (for example, 0.1 g of 1,2,3,4-$^{13}$C$_4$ fumaric acid costs at least 100,000 yen) and stable isotope-labeled tartaric acid is not available on the market.

Various methods for synthesizing isotope-labeled fumaric acid were so far reported. For example, there are known a method wherein a malonic ester is synthesized (E. C. Jorgensen et al., J. Am. Chem. Soc., 74, 2418, 1952), a method wherein a reaction for leaving dibromosuccinic acid is employed (R. F. Nystrom et al., J. Am. Chem. Soc., 74, 3434, 1952) and a method wherein the reduction of acetylenedicarboxylic acid is employed in the course of the reactions (Y. J. Topper et al., J. Biol. Chem. 177, 303, 1949).

For synthesizing stable isotope-labeled tartaric acid, for example, dihydroxylation of fumaric acid by the oxidation with osmium is known (H. Erlenmeyer et al., Helv. Chim. Acta, 22, 701, 1939; and E. C. Jorgensen et al., J. Am. Chem. Soc., 74, 2418, 1952).

However, those known methods have problems that they are unsuitable for the large-scale production of stable isotope-labeled fumaric acid or tartaric acid and that according to those methods is difficult to control the regio-selectivity. For example, methods of E. C. Jorgensen et al. and R. F Nystrom et al. for synthesizing stable isotope-labeled fumaric acid are both suitable for the synthesis in a small scale, but the increase in the scale is difficult. Further, a method of Y. J. Topper is unsuitable for the synthesis of asymmetric fumaric acid such as 1-$^{13}$C fumaric acid or 2-$^{13}$C fumaric acid while it is suitable for the synthesis of labeled symmetric fumaric acid such as 1,4-$^{13}$C$_2$ fumaric acid, 2,3-$^{13}$C$_2$ fumaric acid or 1,2,3,4-$^{13}$C$_4$ fumaric acid.

In the method of H. Erlenmeyer et al. for synthesizing labeled tartaric acid, the obtained tartaric acid is racemic and, therefore, the optical resolution is necessary for isolating L-tartaric acid or D-tartaric acid. This method cannot be easily accepted as a useful method wherein the expensive, stable isotope is used because the yield of the product is reduced by the optical resolution.

SUMMARY OF THE INVENTION

The object of the present invention is to achieve the replacement with deuterium in protein without damaging the NMR sensitivity of the other hydrogen nuclei and also to achieve the rapid analysis of NMR spectra of protein having a molecular weight far higher than that in the prior method and the high-performance determination of the stereostructure.

Another object of the present invention is to provide a combination of a stable isotope-labeled amino acid suitably usable for method for NMR structure analysis of a target protein by the NMR spectra determination with a stable isotope-labeled amino acid constituting the target protein.

Still another object of the present invention is to provide a method for incorporating a stable isotope-labeled amino acid(s) into a target protein.

A further object of the present invention is to provide an NMR method for analyzing the structure of a protein.

Another object of the present invention is to provide a general-purpose method for synthesizing regio-selective, stable, isotope-labeled fumaric acid having any of all label patterns at a relatively low cost.

Another object of the present invention is to provide a method for synthesizing stable isotope-labeled tartaric acid of a high chemical purity from the stable isotope-labeled fumaric acid obtained as described above.

The above-described objects and other objects of the present invention will be apparent from the following description and Examples.

The above-described problems can be solved by the present invention. At first, the present invention provides a stable isotope-labeled amino acid which is at least one of amino acids constituting a protein and which has at least one of the following labeling patterns:
(a) hydrogen atoms except at least one hydrogen atom in one or more methylene groups are deuterated,
(b) hydrogen atoms in one of prochiral gem-methyl groups are completely deuterated,
(c) hydrogen atoms in prochiral methyl groups are partially deuterated, and
(d) all hydrogen atoms except one of them in methyl group are deuterated and hydrogen atoms in the aromatic ring are partially deuterated.

In the first invention, it is preferred that all carbon atoms having the remaining hydrogen atoms in methylene group and/or methyl group are replaced with $^{13}C$. It is also preferred that all nitrogen atoms are replaced with $^{15}N$.

Secondly, the present invention provides a method for incorporating the above-described stable isotope-labeled amino acid(s) into a target protein, which is characterized by incorporating the above-described stable isotope-labeled amino acid into a target protein by cell-free protein synthesis system.

Thirdly, the present invention provides a method for NMR analysis of the structure of protein by incorporating the above-described isotope-labeled amino acid(s) into the target protein and determining NMR spectra to analyze the structure.

Fourthly, the present invention provides a method for producing regio-selectively stable isotope-labeled fumaric acid, which comprises coupling stable isotope-labeled acetic acid with stable isotope-labeled bromoacetic acid.

Fifthly, the present invention provides a process for producing regio-selectively stable isotope-labeled fumaric acid, which comprises tert-butyl-esterifying stable isotope-labeled acetic acid and stable isotope-labeled bromoacetic acid, oxidatively coupling them and hydrolyzing the product with an acid.

In the fifth invention, preferably, stable isotope-labeled acetic acid and stable isotope-labeled bromoacetic acid are brought into contact with liquefied isobutene in the presence of an acid catalyst to convert the stable isotope-labeled acetic acid and stable isotope-labeled bromoacetic acid into tert-butyl esters thereof.

The sixth invention provides a method for producing regio-selectively stable isotope-labeled fumaric acid, which comprises the steps of converting tert-butyl acetate obtained from stable isotope-labeled acetic acid into enolate thereof, adding tert-butyl bromoacetate obtained from stable isotope-labeled bromoacetic acid thereto in the presence of an organoselenium compound, oxidizing the obtained compound and hydrolyzing the product.

The seventh invention provides a method for producing stable isotope-labeled tartaric acid, which comprises the steps of oxidizing the stable isotope-labeled fumaric acid obtained by the above-described method with an asymmetric dihydroxylating agent and hydrolyzing the obtained product.

In the seventh invention, the asymmetric dihydroxylating agent is preferably selected from the group consisting of AD-mix-α and AD-mix-β.

BRIEF DESCRIPTION OF THE DRAWINGS

FIG. 10 shows the results of a simulation of the calculation of the structure of lysozyme.

FIG. 12 shows $^1H$-$^{13}C$ CT-HSQC spectra of calmodulin protein synthesized by using the combination of SAIL amino acids shown in FIG. 11.

DETAILED DESCRIPTION OF THE INVENTION

Figures 1A, 1B:
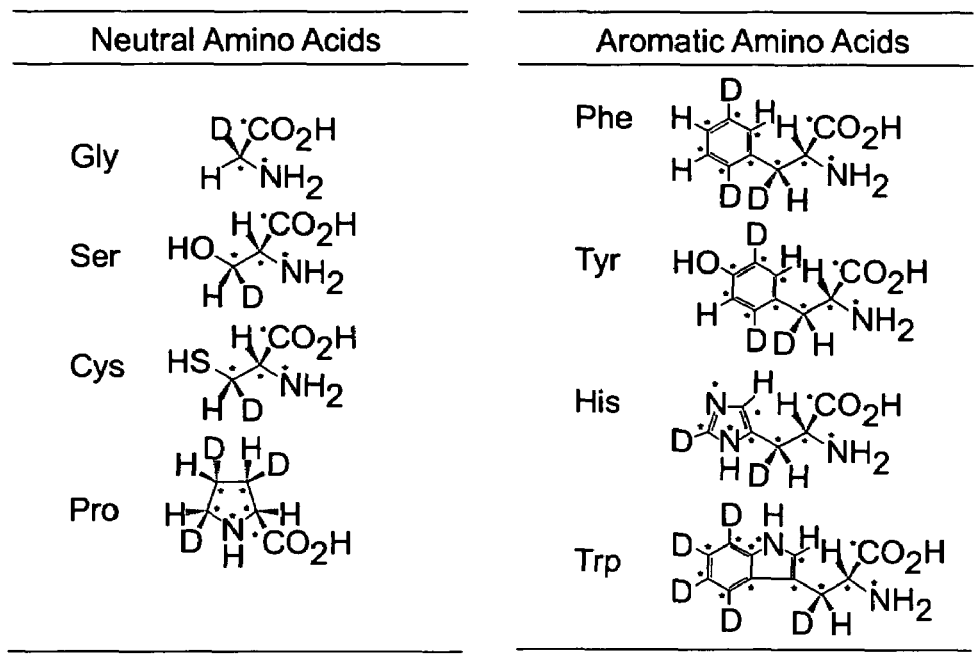
FIG. 1 shows the structures of designed deuterides of 20 amino acids constituting protein.

The present invention is characterized as described above, and the mode for carrying out the invention will be described below.

It is to be emphasized that the most important point in the NMR analysis of the stable isotope-labeled amino acids and protein containing them in the present invention is as follows: hydrogen at a specified position in a specified steric environment is strictly selected and deuterated unlike a conventional technique wherein the deuterium exchange of amino acid is conducted at random. By this technique, hydrogen atoms unnecessary for the determination of the structure are completely deuterated, while the sensitivity of necessary hydrogen atoms is not lowered at all. As a result, unnecessary signals disappeared, the accuracy of the obtained stereostructure is improved and the time required for the signal analysis and structure determination is remarkably shortened.

Various techniques can be employed for the deuteration and chemical synthesis of the labeled amino acids in the present invention. For example, they can be chemically synthesized according to a reaction scheme which will be shown in Examples given below.

The stable isotope-labeled amino acid(s) thus prepared is then incorporated into a target protein for the structure analysis of the protein by NMR.

Any one or more of the amino acids constituting protein or all of them can be replaced with stable isotope-labeled amino acid(s) having a pattern capable of making the obtainment of the stereostructure information and NMR spectra analysis most effective. The technique of preparing a protein for this purpose may be any of a technique for synthesizing ordinary high-expression protein with cultured biological cells, a technique for synthesizing peptides and protein by the organic chemistry or enzyme chemistry, or a technique for obtaining a protein by using a cell-free extract. The control of the isotopic dilution and diffusion by the amino acid metabolism is easy in the present invention, while they were not easy and they posed problems in the ordinary technique wherein cultured biological cells were used. It is made possible by the present invention that labeled amino acids, which cannot be easily synthesized in a large amount, can be highly efficiently incorporated into protein. In view of those facts, the method for synthesizing a protein by using the cell-free extract is very excellent and suitable for the purpose of the present invention. However, this fact does not deny the practical value of other techniques.

Various techniques may be employed for the spectral determination by NMR and also for the structure analysis of protein. It is also possible to specify the changed position in the structure by the ligand bond.

Anyway, the most important characteristic feature of the present invention resides in that amino acids used herein have various deuterium-labeled patterns. The main point of the present invention is that by incorporating those amino acids into protein, advantages which could not be obtained in the prior method can be obtained in the analysis of the stereostructure of the protein. It is thus indispensable for understanding the outline of the present invention to clearly define the various deuterium-labeled patterns. The definition of each pattern of the deuteration will be described below.

Stereo-Selective Deuteration (SSD):

Even when one of methylene protons, i.e. gem-methyl groups (for example, two prochiral methyl groups of Val and Leu), of amino acids is completely erased from the spectra by the deuteration, a necessary stereostructure information can be obtained from the steric assignment (pro-R, pro-S) information of the other proton (remaining proton) and the tetrahedrality in the surroundings of carbon atom. In this case, it is preferred to keep carbon atom of methyl group to be erased to simplify the spin system. It is also possible to obtain accurate information of branched amino acids such as Val, Leu and Ile in the signal assignment of a side chain by ordinary magnetization in which the magnetic charge weakens in the course of starting from the main chain till the detection in the side chain.

Regio-Selective Deuteration, RSD:

When the spin system of a side chain of an amino acid is complicated, the spin system can be remarkably simplified by selectively deuterate a specific position to remarkably easily obtain the information of the stereostructure of the protein.

Stereo-Array Deuteration, SAD:

When two or more prochiral centers are present, an extremely large number of isotopomers are produced by the ordinary deuteration to seriously lower the sensitivity and accuracy in the determination of the structure information. In such a case, only single isotopomer can be realized by stereo-selective deuteration while the stereo-chemical inter-relationship between new chiral centers formed by the deuteration is kept. This new labeled pattern will be called "stereo-array deuteration" hereinafter.

Proton-Density Minimization, PDM:

Hydrogen atoms in methyl group, aromatic ring, etc. are magnetically equivalent. Therefore, they have protons having Surplus structure information. The proton density in protein can be minimized by deuterating all protons ($CH_3 \rightarrow CHD_2$ or the like), leaving necessary and minimum protons. This technique is called the proton-density minimization.

According to the definitions described above, the stable isotope-labeled amino acids practically have the following labeling patterns as described above in the first mode of the present invention:
(a) hydrogen atoms except at least one hydrogen atom of one or more methylene groups are stereo-selectively deuterated (CDH),
(b) hydrogen atoms in one of prochiral gem-methyl groups are completely deuterated ($CD_3$),
(c) hydrogen atoms in prochiral methyl groups are partially deuterated ($CDH_2$, $CD_2H$), and
(d) all hydrogen atoms except one of them in methyl group are deuterated ($CD_2H$) and hydrogen atoms in the aromatic ring are partially deuterated.

By combining the deuteration techniques classified as described above, amino acids optimum for obtaining information of stereostructure of protein can be designed. In the deuteration of methylene group and methyl group in the present invention, as described above, it is preferred from the viewpoint of NMR determination technique that all carbon atoms having hydrogen atoms which remain after the main chain and side chain signal assignment are replaced with $^{13}C$ and that all nitrogen atoms constituting amino acids are replaced with $^{15}N$. On the other hand, when hydrogen atoms are to be completely removed as $CD_3$, it is advantageous to leave carbon as $^{12}C$ so that no spin coupling is contained between $^{13}C$—$^{13}C$. The term "assignment" herein indicates the position of the residue, from which the signal is derived, in the amino acid sequence.

In the first mode described above, it is preferred that in the stable isotope-labeled amino acids, all amino acids constituting the target protein are used in the form of a combination of stable isotope-labeled amino acids constituting the target protein and having the following label patterns:
(a) when methylene group having two hydrogen atoms is present, one of methylene hydrogen atoms is deuterated,
(b) when prochiral gem-methyl groups are present, all hydrogen atoms in one methyl group are completely deuterated and hydrogen atoms in the other methyl group are partially deuterated,
(c) when methyl group other than those stated above is present, all hydrogen atoms except one of them in the methyl group are deuterated or all hydrogen atoms in the methyl group are deuterated,
(d) when the aromatic ring has hydrogen atoms, the hydrogen atoms in the aromatic ring may be partially deuterated,
(e) after the deuteration in above (a), (b) and (c) all carbon atoms of hydrogen atom-containing methylene group and/or methyl group are replaced with $^{13}C$, and
(f) all nitrogen atoms are replaced with $^{15}N$.

Further, when the aromatic ring has hydrogen atoms, these hydrogen atoms are preferably partially deuterated. It is preferred that (e) after the deuteration in above (a), (b) and (c), all carbon atoms in hydrogen atom-containing methylene group and methyl group are converted into $^{13}C$. It is also preferred that carbon atoms constituting carbonyl group and guanidyl group in amino acids are replaced with $^{13}C$. Preferably, all carbon atoms bonded with $^{1}H$ are completely replaced with $^{13}C$.

Figures 1C, 1D:
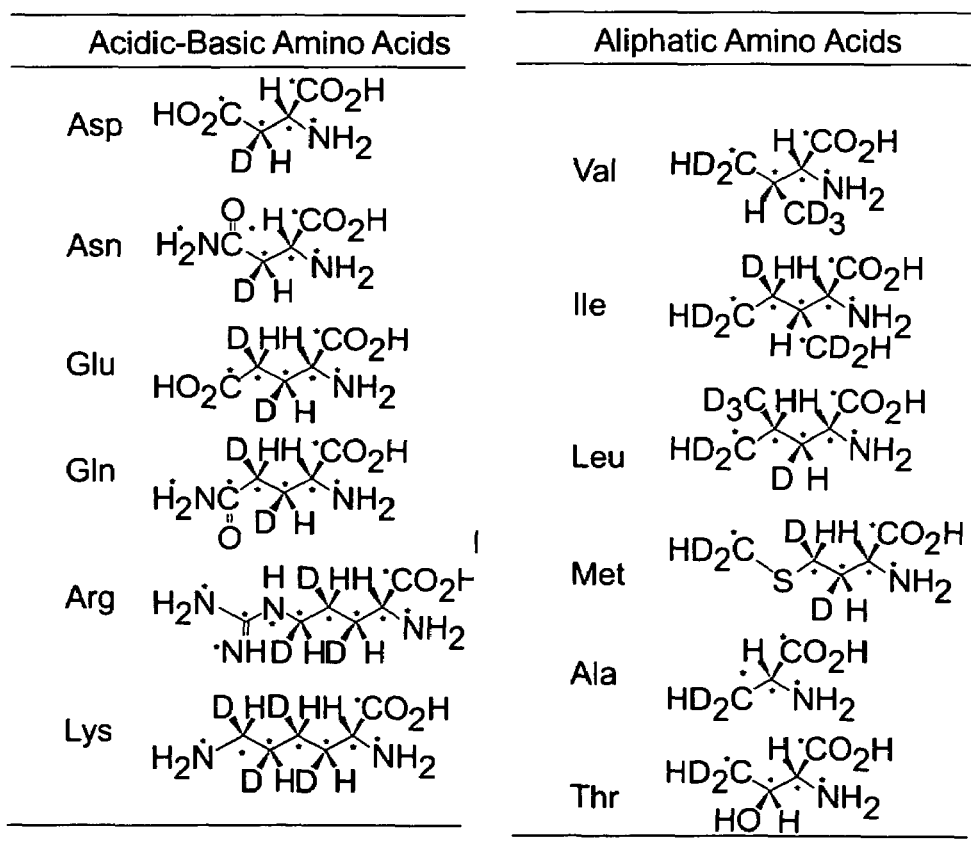

FIG. 1 shows structures of 20 stable isotope-labeled amino acids designed from the amino acids constituting protein by combining all of these techniques. The target of the patterns shown in FIG. 1 is the application of them to the determination of the stereostructure of protein. Further, various designs are also possible according to the necessary structure information or properties of the target protein.

For the incorporation of stable isotope-labeled amino acids into the target protein in the second mode of the present invention, a preferred method comprises cell-free protein synthesis system by using a combination of the above-described stable isotope-labeled amino acids as the whole amino acids constituting the target protein to prepare the target protein comprising the stable isotope-labeled amino acids.

For analyzing the structure of protein by NMR in the third mode of the present invention, a preferred method is that for analyzing NMR structure of a target protein, which comprises analyzing the structure of a target protein in which all amino acids constituting the target protein are replaced with the above-described stable isotope-labeled amino acids by NMR spectral determination.

For preparing the regio-selective stable isotope-labeled fumaric acid in the fourth mode of the present invention, the stable isotope-labeled acetic acid and stable isotope-labeled bromoacetic acid used as the starting materials may be of any labeling pattern or, in other words, they may have the stable isotope in any position. Further, the position into which the stable isotope is to be introduced and the number of the stable isotopes are not limited. Namely, two or more stable isotopes may be incorporated thereinto. The stable isotope-labeled acetic acids are, for example, [1-$^{13}C$] acetic acid, [2-$^{13}C$] acetic acid, [1,2-$^{13}C_2$] acetic acid, [2-$^{2}H_3$; 1-$^{13}C$] acetic acid, [2-$^{2}H_3$; 2-13C] acetic acid and [2-$^{2}H_3$; 1,2-$^{13}C_2$] acetic acid. The stable isotope-labeled bromoacetic acids are, for example, [1-$^{13}C$] bromoacetic acid, [2-$^{13}C$] bromoacetic acid, [1,2-$^{13}C_2$] bromoacetic acid, [2-$^{2}H_3$; 1-$^{13}C$] bromoacetic acid, [2-$^{2}H_3$; 2-$^{13}C$] bromoacetic acid, [2-$^{2}H_3$; 1,2-$^{13}C_2$] bromoacetic acid. By coupling them, the synthesis of fumaric acid of any labeling pattern is made possible.

The coupling of the stable isotope-labeled acetic acid and the stable isotope-labeled bromoacetic acid is carried out after tert-butyl-esterifying them. The method for the tert-butyl-esterification is not particularly limited. For example, acetic acid can be esterified by known methods such as a method wherein tert-butyl alcohol and calcium carbide are used [chemical formula (I)] described in R. V. Oppenauer, et al., Monatsh, Chem. 97, 62, 1966 and R. S. Monson, "Advanced Organic Synthesis, Methods and Techniques", Academic, 1971, p. 62; a method wherein tert-butyl alcohol and acetyl chloride are used [chemical formula (II)] described in B. Abramovich, et al., J. Am. Chem. Soc., 65, 989, 1943; and a method wherein ketone and tert-butyl alcohol are used [Chemical formula (III)] described in C. D. Hurd, et al., J. Am. Chem. Soc., 61, 3355, 1939.

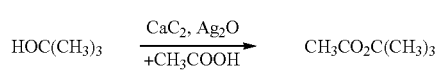
(I)

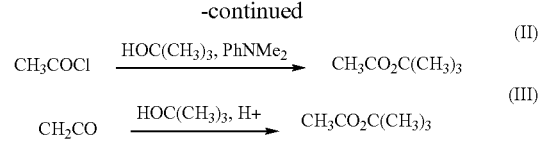

On the other hand, bromoacetic acid can be esterified by an ordinary method such as a method of any of following chemical formulae (IV) to (VI):

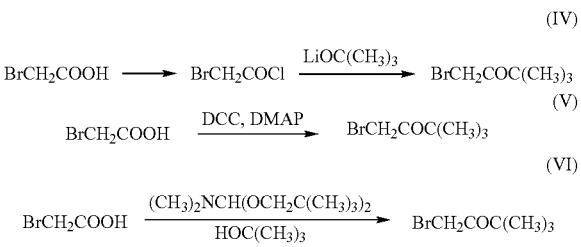

In the present invention, a method which is easy and most preferred comprises hermetically containing each of the stable isotope-labeled acetic acid and the stable isotope-labeled bromoacetic acid with liquefied isobutene in the presence of an acid catalyst in a reaction apparatus and stirring them at room temperature. Although the acid catalyst used in this method is not particularly limited, various ion exchange resins are preferably used as the catalyst fixed on a carrier because such a catalyst can be easily removed (see, for example, J. Chem. Soc., Perkin Trans. 1, 3815–4195, 2000). Concrete examples of those resins include sulfonic acid type cation exchange resins [for example, Dowex (registered trade name) W-X8 of Dow Co. and Amberlyst (registered trade name) R15 of Rohm Haas Co.]. These cation exchange resin catalysts can be easily removed by the filtration.

In this reaction, the reaction conditions such as the amount of isobutene and catalyst, temperature and time are not particularly limited. For example, when acetic acid is tert-butyl-esterified in the presence of Amberlyst (registered trade name) R 15, the amount of isobutene is at least 1 equivalent per equivalent of acetic acid. When isobutene is used in an amount of 3 equivalents, a high yield can be obtained after the reaction. The amount of Amberlyst (registered trade name) R 15 may be at least 1 wt. %. Even when Amberlyst R15 is used in an amount of 1 wt. %, the tert-butyl esterification proceeds to form a sufficiently high yield of the product. The reaction temperature may be as low as 0° C. to around room temperature. Under these conditions, the reaction is completed within 3 hours and the t-butyl esterification reaction proceeds to bring a yield of as high as at least 90%. Therefore, the product can be used in the subsequent step without the purification.

The stable isotope-labeled tert-butyl acetate and stable isotope-labeled tert-butyl bromoacetate obtained as described above can be coupled by various organic synthesis reactions. The methods are, for example, a method (VII) wherein an acetic acid ester is oxidatively dimerized as described in Leo A. Paquette et al., J. Org. Chem., 60, 7277, 1995, and a method (IX) wherein an acetic acid ester is iodized and then converted into a succinic ester (VIII) and then this ester is converted into fumaric acid with various reagents (IX).

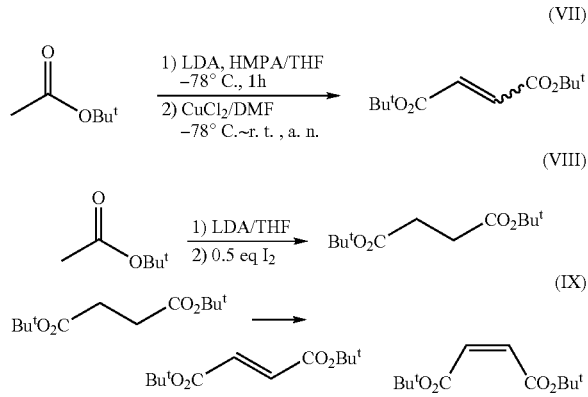

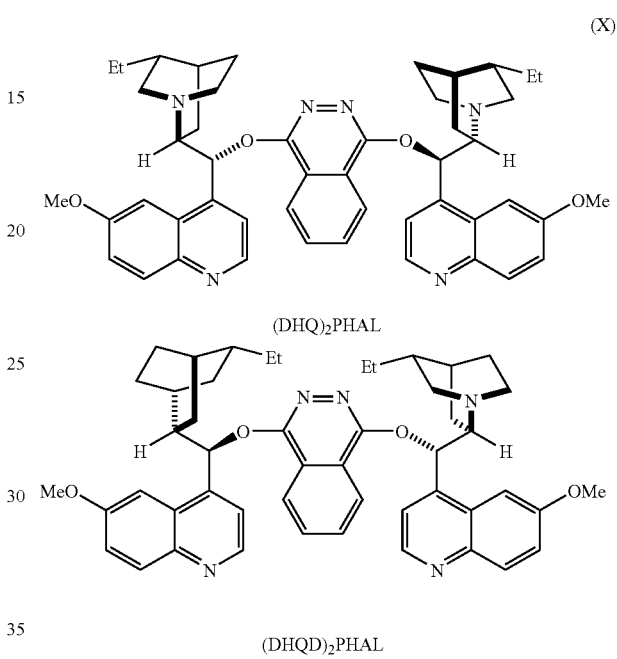

Preferably, a method for synthesizing a succinic acid derivative though a selenenyl intermediate is employed. Concretely, stable isotope labeled tert-butyl acetate is converted into a corresponding enolate. Namely, this compound is brought into contact with strongly basic lithium diisopropylamide (LDA) to form a corresponding lithium enolate. An organoselenium compound such as phenylselenenyl chloride, phenylselenenyl bromide or phenylselenenyl iodide is added thereto. Then stable isotope-labeled tert-butyl bromoacetate is added to the reaction mixture to obtain di-tert-butyl 2-phenylselenenylsuccinate. Although LDA may be replaced with lithium hexamethyldisiloxane (LiHMDS), sodium hexamethyldisiloxane (NaHMDS) or butyl lithium (n-BuLi), the reaction proceeds to obtain a high yield when LDA is used.

Because both LDA ($LiN(CH(CH_3)_2)_2$) and phenylselenenyl chloride ($C_6H_5SeCl$) used herein violently react with water, the reaction is desirably carried out under dehydration conditions in an inert gas atmosphere such as nitrogen or helium atmosphere. The reaction is preferably conducted in a solution in a suitable organic solvent such as THF, DME, ether, DMPU (N,N'-dimethylpropyleneurea).

Di-tert-butyl 2-phenylselenenylsuccinate obtained by the above-described reaction method is oxidized to obtain di-tert-butyl fumarate. The oxidation method is not limited, and various well-known methods can be employed. Preferably, peroxide such as m-chloroperbenzoic acid or hydrogen peroxide is used. The oganoselenium compounds are made water-soluble by oxidizing them again with hydrogen peroxide or the like, and the water soluble compounds can be removed by washing with water. The stable isotope-labeled fumaric acid can be obtained by hydrolyzing di-tert-butyl fumarate with an acid such as hydrochloric acid or sulfuric acid.

As a matter of course, when the intended compound is a stable isotope-labeled fumaric ester derivative, this compound may be synthesized from tert-butyl fumarate by various organic synthesis techniques without the hydrolysis in the last step.

The present invention also provides a method for obtaining stable isotope-labeled tartaric acid from the stable isotope-labeled fumaric acid obtained as described above. In this method, regio-selectively stable isotope-labeled fumaric acid is converted into diethyl fumarate and then the ester thus obtained is asymmetrically dihydroxylated to obtain diethyl tartrate.

In this step, diethyl fumarate can be obtained by bringing thionyl chloride into contact with fumaric acid and dissolving the product in diethyl ether. As the asymmetric dihydroxylating reagent, for example, osmium oxide having various ligands as described in Hartmuth C. Kolb et al., Chem. Rev., 94, 2483, 1994 can be used. In particular, AD-mix-α and Ad-mix-β developed by K. B. Sharpless et al. are preferably used. Both AD-mix-α and Ad-mix-β contain potassium osmate, potassium hexacyanoferrate (III), potassium carbonate and chiral ligand $(DHQ)_2PHAL$ or $(DHQD)_2PHAL$ (chemical formula (X)).

As a matter of course, known or new asymmetric dihydroxylating agents can be used in addition to those described above. According to the chirality of the asymmetric dihydroxylating agent used, either D-diethyl tartrate or L-diethyl tartrate is selectively used. For example, when AD-mix-β is used, diethyl L-tartrate having an optical purity of as high as 99% or higher is obtained. Diethyl tartrate thus obtained is hydrolyzed to obtain stable isotope-labeled tartaric acid.

As a matter of course, when the intended compound is a stable isotope-labeled tartaric ester derivative, the intended compound can be synthesized from diethyl tartrate by various organic synthesis techniques without the final hydrolysis step.

As described above, the reaction proceeds at a low temperature of not higher than room temperature in a relatively short time in all the steps in the process of the present invention for producing stable isotope-labeled fumaric acid and stable isotope-labeled tartaric acid. Further, the yield is as high as at least 60 to 90% in all the reaction steps. In addition, stable isotope-labeled acetic acid used as the starting material is relatively inexpensive (for example, about 5,000 yen/10 g to about 60,000 yen/g) depending on the position of the labeling. Thus, the process of the present invention is useful for synthesizing regio-selectively synthesizing stable isotope-labeled fumaric acid or stable isotope-labeled tartaric acid on a large scale.

The following Examples illustrate the preparation of protein labeled with amino acids having various labeling patterns, and they also prove the fact that NMR spectra of each of them has very excellent characteristics in obtaining the stereostructure.

It is to be noted that the following Examples are only for the concrete understanding of the present invention and the Examples are not for limiting the scope of the invention.

EXAMPLES

Example 1

Preparation of Protein Containing SSD-Glycine Incorporated thereinto and NMR Determination Steps 1 to 12 illustrate the synthesis of stereo-selectively mono-deuterated (2S)-[1,2-$^{13}$C$_2$;2-$^{15}$N;2-$^2$H]glycine (hereinafter referred to as SSD-glycine) according to the following scheme 1:

Scheme 1

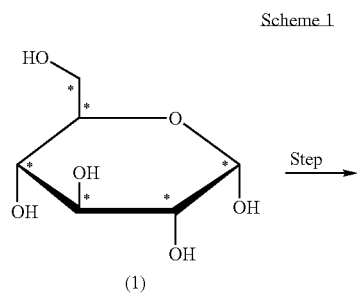
(1)

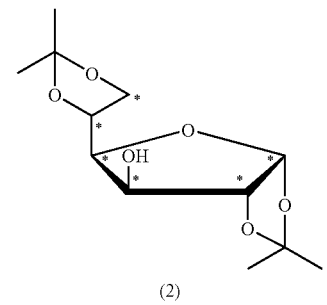
(2)

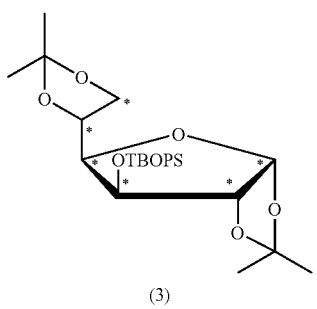
(3)

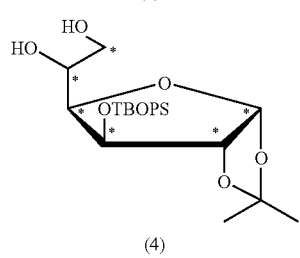
(4)

-continued

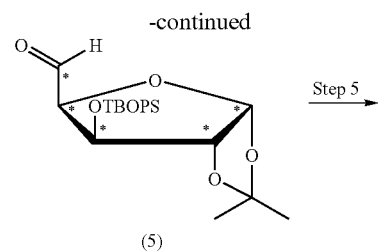
(5)

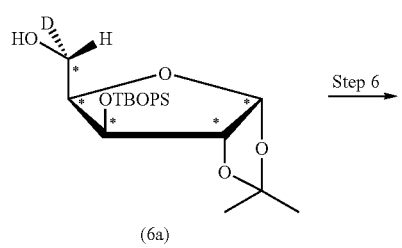
(6a)

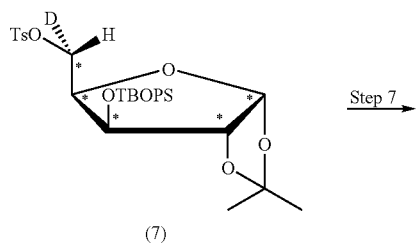
(7)

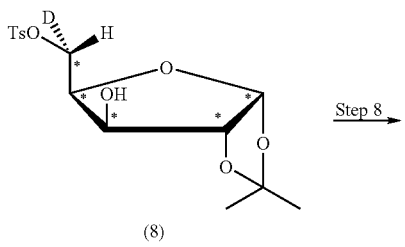
(8)

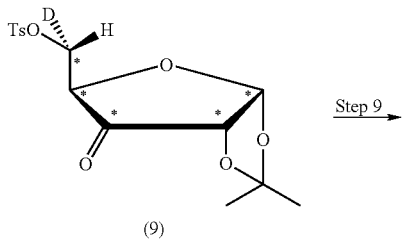
(9)

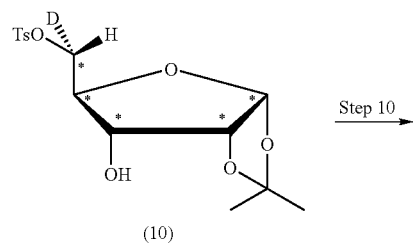
(10)

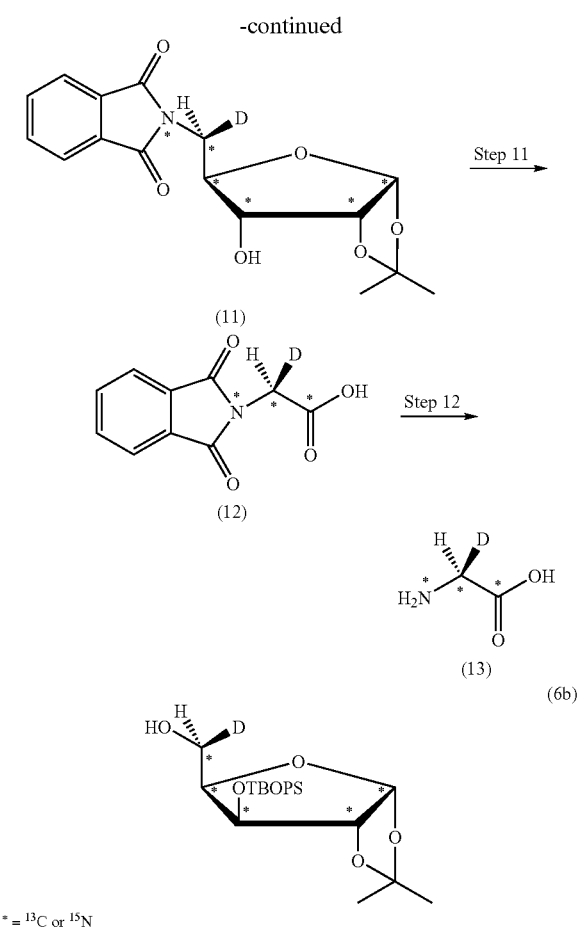

* = $^{13}C$ or $^{15}N$

<Step 1>

Compound (2) (12.55 g, 48.2 mmol, 87%) was obtained from [ul-$^{13}C_6$]-glucose (10.06 g, 55.8 mmol) (1) with reference to a method disclosed in a literature (K. P. R. Kartha et al., Tetrahedron Lett., 27, 3415, 1986).

<Step 2, Step 3 and Step 4>

Compound (2) (12.55 g, 48.2 mmol) was converted to compound (3) (22.08 g, 44.3 mmol) by a method disclosed in a literature (Nicolaou et al., J. Am. Chem. Soc., 110, 4673, 1988). 300 ml of 80% acetic acid was added to compound (3) to obtain a solution. After removing the protecting group at 75° C. for 3 hours, the reaction mixture was cooled to room temperature and then concentrated under reduced pressure. The azeotropic process with ethanol was repeated 4 times to obtain compound (4). Then intended compound (5) (12.9 g, 30.2 mmol) was obtained in a yield of 68% from compound (2) by a method described in a literature (C. Hubschwerlen et al., Synthesis. 962, 1986).

<Step 5>

150 ml of methylene chloride was added to compound (5) (3.66 g, 8.58 mmol) to obtain a solution. Silica gel (73.8 g) and tributyltin deuteride (5.0 g, 7.2 mmol) were added to the solution, and they were stirred for 18 hours. A silica gel column was charged with the reaction mixture. Organotin compounds were eluted with 1 L of methylene chloride and then compound (6a) (3.13 g, 7.29 mmol) was obtained in a yield of 85%.

<Step 6 and Step 7>

Compound (6a) was tosylated at the 5-position with reference to a method described in a literature (Joseph A. Tino et al., J. Med. Chem. 36, 1221, 1993). The obtained compound (7) was dissolved in 83 ml of tetrahydrofuran. 1 M tetrabutylammonium fluoride/tetrahydrofuran solution (13.9 ml, 13.9 mmol) was added to the obtained solution, and they were stirred at room temperature for 15 minutes. The reaction mixture was purified by the silica gel column chromatography with hexane/ethyl acetate=1/1 to obtain compound (8) (2.73 g, 7.79 mmol, 67%).

<Step 8>

Compound (8) (2.22 g, 6.34 mmol) was dissolved in 110 ml of methylene chloride, and the obtained solution was cooled to 0° C. Dess-Martin reagent (8.05 g, 18.99 mmol) was added to the solution, and they were stirred while the temperature was kept at 0° C. The temperature was elevated to room temperature, and the obtained mixture was stirred for 1.5 hours. 40 ml of saturated sodium hydrogencarbonate solution containing 6 g of sodium thiosulfate and 50 ml of ethyl acetate were added to the reaction mixture, and they were stirred for 5 minutes. After washing with 50 ml of saturated sodium hydrogencarbonate solution twice, with 50 ml of water once and with 50 ml of brine once, the organic layer was dried over sodium sulfate and then concentrated under reduced pressure to obtain compound (9).

<Step 9>

A solution of compound (9) in 75 ml of methanol was cooled to 0° C. A solution of sodium borohydride (120 mg, 3.17 mmol) in 50 ml of methanol was added thereto. 2 minutes after, the reaction mixture was taken from the ice bath and stirred for 1.5 hours. 80 ml of acetone was added to the reaction mixture, and they were stirred for 5 minutes. 20 ml of water was added thereto. After the concentration under reduced pressure, 40 ml of ethyl acetate was added to the reaction mixture and they were washed with water (40 ml×1) and brine (40 ml×1). The organic layer was dried over sodium sulfate and then concentrated under reduced pressure to obtain compound (10).

<Step 10>

Compound (10) was dissolved in DMF. After the nitrogen replacement, potassium phthalimide (1.76 g, 9.51 mmol) was added thereto. The obtained mixture was stirred at 70° C. for 10 hours, concentrated and purified by the silica gel column chromatography with hexane/ ethyl acetate=1/1 to obtain compound (11).

<Step 11>

Compound (11) was dissolved in a solvent mixture of 50 ml of acetic acid and 50 ml of 5 N sulfuric acid, and the obtained solution was stirred at 65° C. for 1 hour. After cooling to room temperature, $KMnO_4$ (4.15 g, 26.11 mmol) was added to the reaction mixture and they were stirred at room temperature for 3 hours. Sodium thiosulfate was added to the reaction mixture until the mixture became colorless. Then 20 ml of water was added thereto. After the extraction with methylene chloride (30 ml×3), the organic phase was washed with water (20 ml×2), dried over sodium sulfate and concentrated under reduced pressure to obtain compound (12).

<Step 12>

Compound (12) was refluxed in 50 ml of 1 N hydrochloric acid. After cooling, white needle-like crystals thus formed were taken by the filtration. Th filtrate was purified with Dowex 50W-X8 to obtain SSD-glycine (13a) (391 mg, 94.95 mmol, 78%).

<Synthesis of Compound (6b)>

By converting compound (5) into compound (6b), SSD-glycine (13b) having a reverse configuration at the 2-position can be synthesized.

Namely, compound (5) (5.0 g, 11.72 mmol) was dissolved in diethyl ether (300 ml), and the obtained solution was cooled to 0° C. in argon atmosphere. Magnesium dibromide/diethyl ether complex (17.96 g, 69.54 mmol) was added to the obtained solution, and they were stirred for 5 minutes. lithium tri-tert-butoxyaluminum deuteride (8.88 g, 34.77 mmol) was added thereto, and they were stirred at 0° C. for 4 hours. 30 ml of 1 N hydrochloric acid was added to the reaction mixture at 0° C. and they were stirred for 10 minutes. After the extraction with ethyl acetate (250 ml×4), the organic layer was washed with brine (100 ml×1), dried over magnesium sulfate and concentrated under reduced pressure to obtain compound (6b).

<Preparation of Labeled Protein>

Proline cis-trans isomerase EPP1b (molecular weight: 18 kDa) from *Escherichia coli* was used as the model protein for establishing a process for highly selectively incorporating the above-described SSD-glycine (13a and 13b). In conventional in vivo protein preparation method wherein *E. coli* or the like is used, it was difficult for methylene proton of Gly to control the isotopic dilution or diffusion by the action of serine hydroxymethyl transferase (SHMT) which catalyzes the mutual conversion of glycine and serine. The inventors of the present invention have succeeded in the preparation of isotope-labeled EPP1b {the labels being two kinds of SSD-glycine and (2S)- and (3R)-[1,2-$^{13}C_2$; 1-$^{15}N$; 2-$^2H$]-Gly} by an in vitro protein synthesizing method with S30 cell-free extract (hereinafter referred to as "cell-free protein synthesis system") while a high stereo-selectivity is kept because the protein-synthesizing function is not lowered even by the addition of a sufficient amount of cycloserine known to be an inhibitor for SHMT.

<NMR Determination of Labeled Protein>

Samples for NMR determination were prepared with SSD-glycine-labeled EPP1b under conditions described in a thesis (E. Kariya et al., J. Biomol. NMR 18, 75–76, 2000). The signal assignment of methylene proton of glycine residue was based on the assignment information of main chain NMR signal described in this thesis.

Figure 2A:
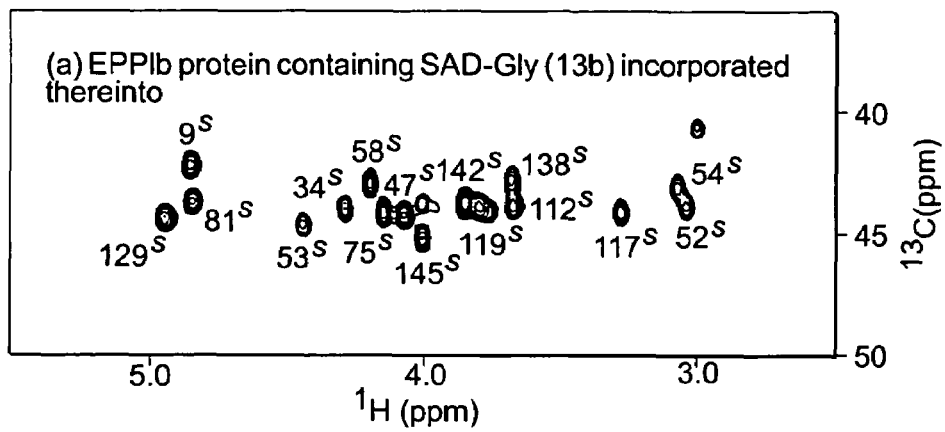
FIG. 2 shows a comparative example of $^1H$-$^{13}C$ HSQC spectra of EPP1b protein (18.2 kDa) containing SSD-glycine incorporated thereinto.
Figure 2B:
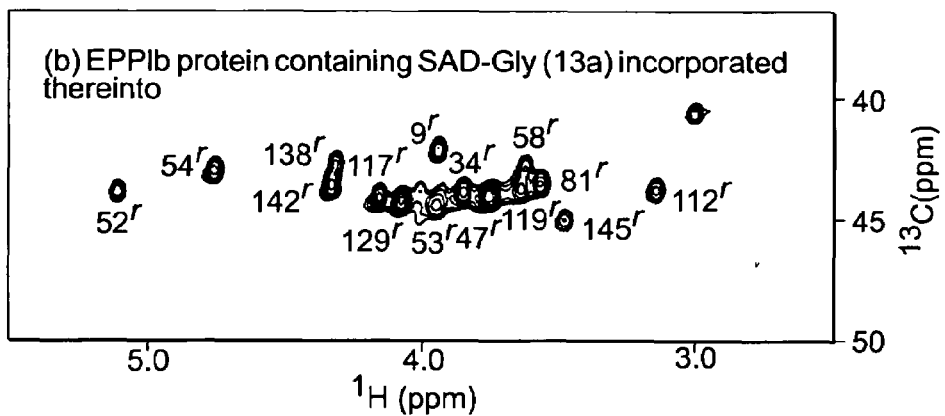
Figure 2C:
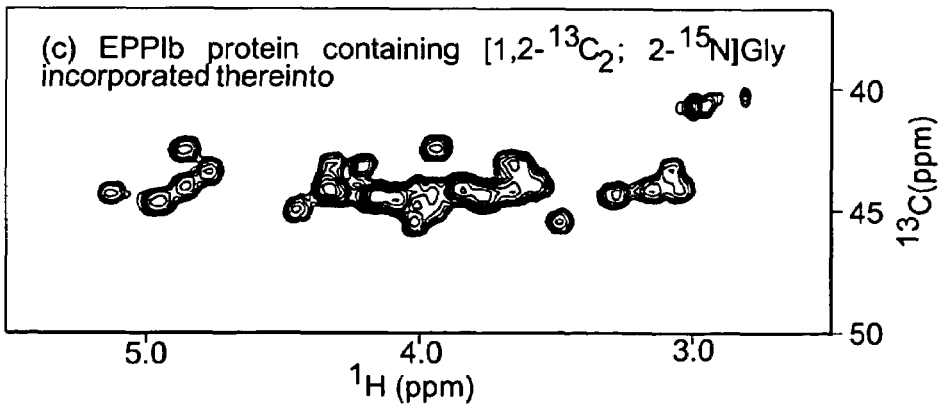

$^1H$-$^{13}C$ HSQC spectra of EPP1b sample having (2S)— and (3R)-[1,2-$^{13}C_2$; 1-$^{15}N$; 2-$^2H$]-glycine incorporated thereinto and that of EPP1b sample having [1,2-$^{13}C_2$; 1-$^{15}N$]-glycine incorporated thereinto are compared with each other in FIG. 2. The following fact is apparent from FIG. 2. In the conventional method wherein a uniformly labeled sample is used, NMR spectra are crowded to make the stereospecific assignment of methylene proton indispensable for the determination of the stereostructure of protein practically impossible. On the other hand, when protein having stereospecifically deuterated SSD-glycine incorporated thereinto is tested, the total number of signals in NMR spectra is reduced to a half and increase in the signal cleavage and increase in the line width due to the spin coupling of methylene protons are is omitted. Thus, in the spectra, glycine-selective labeling is simplified and all the signals can be separately observed on the two-dimensional NMR. In addition, the assignment of stereospecific signals has already been completed in the step of the preparation of the sample and, therefore, the assignment is unnecessary. The important point is that because the stereochemical assignment has already been completed, only one of the two SSD-glycine-labeled protein samples is necessary.

Namely, according to the technique of the present invention, signals unnecessary for the determination of the structure disappeared and the time required for the signal analysis and the structure determination is remarkably shortened.

Example 2

Preparation of Protein Containing SAD-Lysine and NMR Determination

The synthesis of (2S,3R,4R,5S,6R)-[1,2,3,4,5,6-$^{13}C_6$; 2,6-$^{15}N_2$; 3,4,5,6-$^2H_4$]lysine (hereinafter referred to as "SAD-lysine) in steps 13 to 16 will be illustrated according to the following scheme 2:

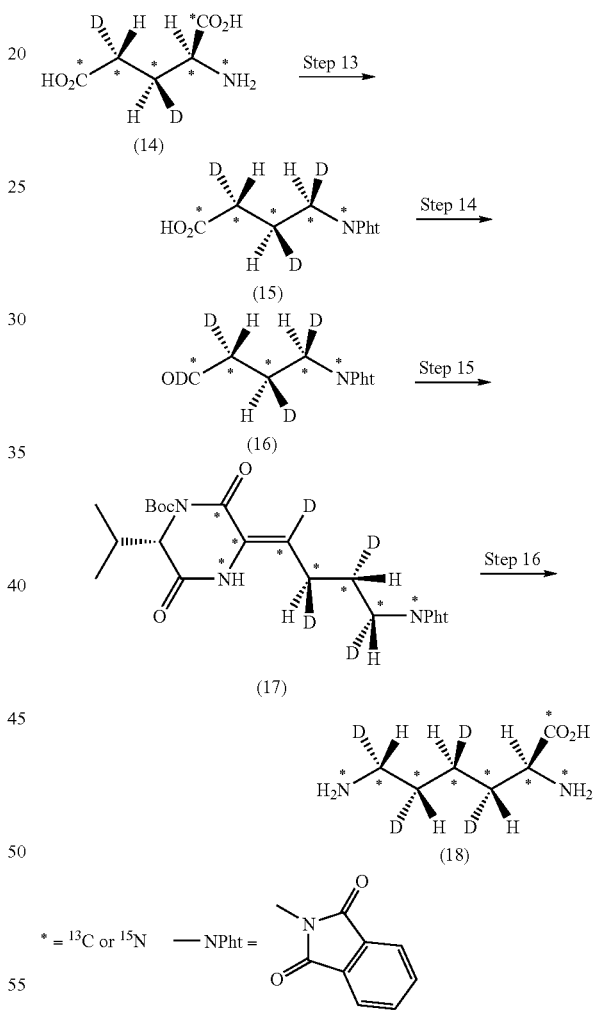

<Step 13>

(2S, 3S, 4R)-[1,2,3,4,5-$^{13}C_5$; 2-$^{15}N$; 3,4-$^2H_2$]glutamic acid (hereinafter referred to as SAD-glutamic acid) (14) (25.02 mmol) derived from uniformly $^{13}C$-labeled L-glutamic acid by a method descried in a literature (M. Oba, et al., J. Org. Chem. 64, 9275, 1999) was dissolved in 0.2 M solution (200 ml) of pyridine hydrochloride in deuterium oxide. The pH of the obtained solution was adjusted at 5 with pyridine containing pyridoxalphosphate (200 mg)

and dithiothreitol (120 mg). Glutamic acid decarboxylase (1000 U, 210 ml) was added to the solution and the obtained mixture was stirred at 37° C. for 3 hours while shielding the light. The obtained reaction mixture was concentrated at a temperature of not higher than 30° C. under reduced pressure. The residue was purified with SK1B. The labeled aminobutanoic acid thus obtained was dissolved in 50 ml of water. Sodium hydrogencarbonate (2.83 g, 26.66 mmol) and N-ethoxycarbonylphthalimide (6.37 g, 29.08 mmol) were added to the obtained solution. The obtained mixture was stirred at room temperature for 1 hour. The reaction solution was adjusted to pH 5 by carefully adding concentrated hydrochloric acid. Crystals thus formed were taken by the filtration. The crystals on the filter paper were washed with cold water and then dried in a vacuum drying vessel to obtain compound (15) (4.43 g, 18.32 mmol, 75%).

<Step 14>

Compound (15) was dissolved in methylene chloride (20 ml). Thionyl chloride (11.9 g, 100 mmol) was added to the obtained solution at room temperature. The obtained solution was stirred at room temperature for 1 hour and then at 40° C. for 2 hours. The reaction solution was concentrated under reduced pressure. The obtained residue was dissolved in benzene. Tetrakistriphenylphosphine palladium (0.21 g, 5 w/w %) and tributyltin deuteride (3.227 ml, 12 mmol) were added to the obtained solution in argon atmosphere, and they were stirred at room temperature for 5 minutes. The reaction mixture was concentrated and then the product was purified by the silica gel column chromatography with hexane/ethyl acetate=7/3 to obtain compound (16) (2.101 g, 9.34 mmol, 93%).

<Step 15>

A solution of a labeled diketopiperazine derivative shown in the figure (1.777 g, 4.95 mmol) and compound (16) (1.013 g, 4.5 mmol) in tetrahydrofuran (45 ml) was cooled to −40° C. under stirring in argon atmosphere. A solution of potassium tert-butoxide (0.616 g) in tetrahydrofuran (45 ml) was added to the solution. The temperature of the reaction solution was slowly elevated to room temperature. Saturated ammonium chloride was added thereto. After the extraction with ethyl acetate, the organic layer was washed with saturated aqueous sodium chloride solution, dried over magnesium sulfate and concentrated under reduced pressure. The residue was purified by the silica gel column chromatography with hexane/ethyl acetate=65/35 to obtain compound (17) (1.270 g, 2.72 mmol, 61%).

<Step 16>

Compound (17) (1.251 g, 2.68 mmol) was dissolved in ethyl acetate (20 ml). Platinum dioxide (0.023 g, 0.1 mmol) was added to the obtained solution and air in the reaction vessel was replaced with deuterium gas. The reaction mixture was stirred at room temperature for 2 hours while the pressure of deuterium gas was kept at 1 kgf/cm². The catalyst was removed by the filtration and the reaction mixture was concentrated. Concentrated hydrobromic acid was added to the reaction mixture and they were stirred at 140° C. for 48 hours. After the concentration under reduced pressure, the product was ion-exchanged with Dowex 50W-X8 to obtain SAD-lysine (18) (0.360 g, 1.73 mmol, 65%).

<Preparation of Labeled Protein>

SAD-lysine-labeled EPP1b was prepared by adding SAD-lysine by a method described in a thesis (E. Kariya et al., J. Biomol. NMR 18, 75–76, 2000).

<Example of NMR Determination of Labeled Protein>

An NMR sample was assigned according to information of the assignment of main chain NMR signals of the protein described in a thesis under conditions described in the same thesis (E. Kariya et al., J. Biomol. NMR 18, 75–76, 2000).

Figure 3A:
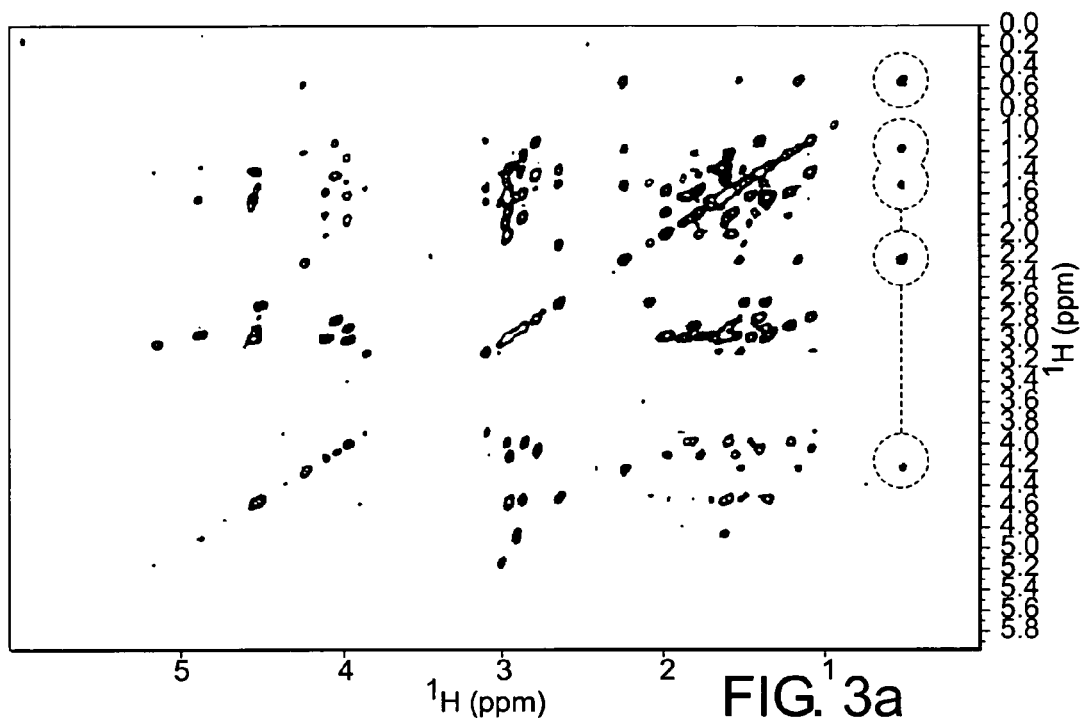
FIG. 3 shows a comparative example of HCCT TOCSY spectra of EPP1b protein (18.2 kDa) containing SAD-glycine incorporated thereinto.
Figure 3B:
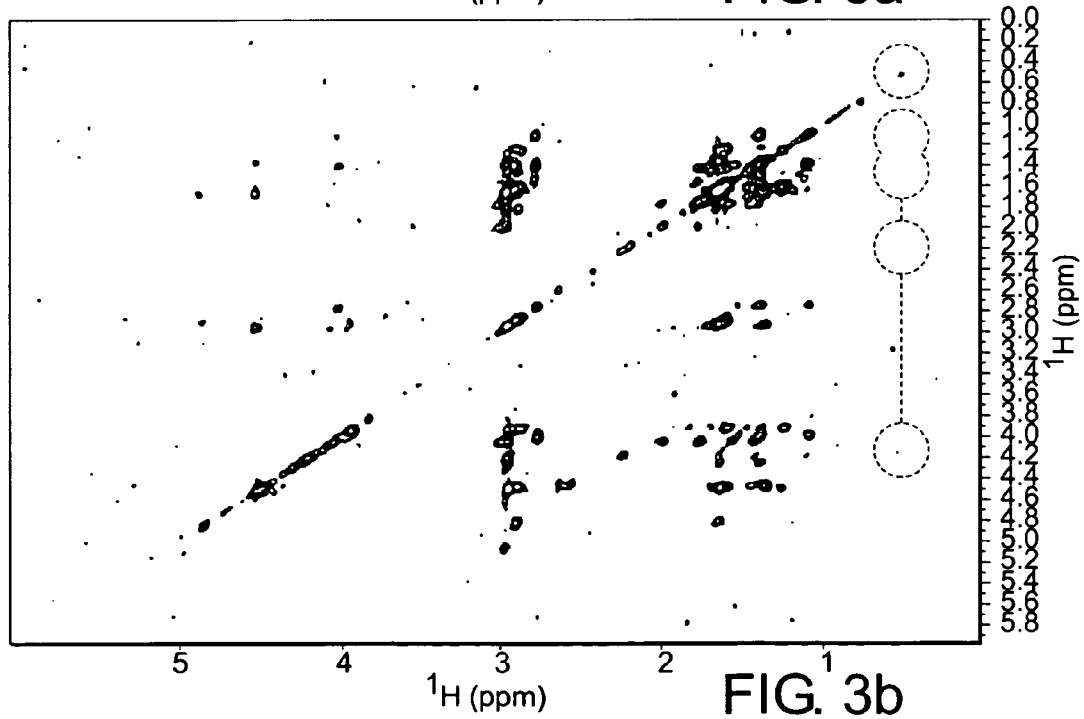

HCCH TOCSY spectra of EPP1b sample containing SAD-lysine incorporated thereinto were determined. FIG. 3 shows the comparison of the results with those of protein containing [ul-$^{13}$C; $^{15}$N]-lysine obtained by an ordinary method. It is apparent from FIG. 3 that protein containing SAD-lysine is more simplified than the protein obtained by the ordinary method. Because the signals of side chains of long-chain amino acids were highly sensitively observed, NMR signals of the side chain of the long-chain amino acids which could not be utilized so far are now utilizable for obtaining the structure information.

Namely, by the technique of the present invention, signals unnecessary for the structure determination disappeared and the sensitivity of the remaining signals is improved. Accordingly, the rapid, reliable signal analysis of a high-molecular weight protein and the determination of the stereostructure thereof with high accuracy are made possible over the range of the prior techniques.

Example 3

Preparation of Protein Containing SAD-Glutamine and NMR Determination Thereof

The synthesis of (2S,3S,4R)-[1,2,3,4,5-$^{13}$C$_5$; 2,5-$^{13}$N$_2$; 3,4-$^2$H$_2$]glutamine (hereinafter referred to as "SAD-glutamine") in step 17 will be illustrated according to the following scheme 3:

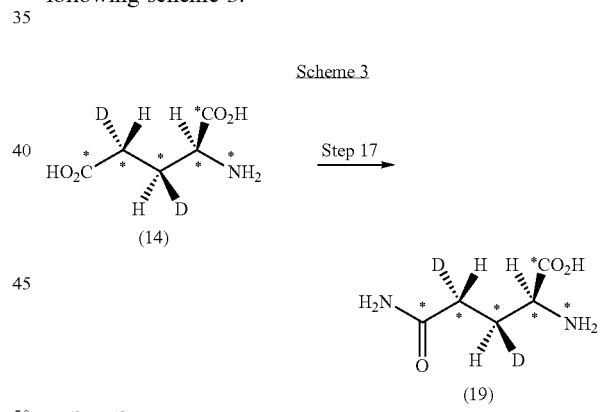

* = $^{13}$C or $^{15}$N

<Step 17>

Concentrated sulfuric acid (55 μl) was added to methanol (1305 μl) and they were cooled to −5 to −10° C. The obtained solution was fed into a 2 ml vial containing SAD-glutamic acid (14) (98 mg, 719 μmol). The obtained mixture was stirred at −4° C. for 1 hour and then at room temperature for 2 hours. After the completion of the stirring, 156 μl of carbon disulfide was added to the reaction mixture while the temperature was kept at 0° C. $^{15}$N-labeled ammonia gas was introduced into the vessel for 14 minutes. After leaving them at room temperature for 10 days, methanol was added thereto and crystals thus formed were taken by the filtration. The filtrate was concentrated and then dissolved in distilled water. After the purification with cation exchange resin DOWEX-50, anion exchange resin IRA96SB and anion exchange resin IRA67 in succession, SAD-glutamine (19) (26 mg) was obtained.

<Preparation of Labeled Protein>

A protein sample containing the above-described SAD-glutamine (19) incorporated thereinto was prepared by adding methionine sulfoximine and 6-diazo-5-oxonorleucine which inhibit enzymes concerning the conversion of SAD-glutamine and glutamic acid—glutamine to EPP1b protein as the model protein under conditions described in a thesis (E. Kariya et al., J. Biomol. NMR 18, 75–76, 2000). Those labeled products could not be prepared by ordinary in vivo protein preparation method because conditions required for inhibiting the metabolic change and for producing protein could not be established.

<Example of NMR Determination of Labeled Protein>

An NMR sample was assigned according to information of the assignment of protein main chain NMR signals described in a thesis under conditions described in the same thesis (E. Kariya et al., J. Biomol. NMR 18, 75–76, 2000).

Figure 4A:
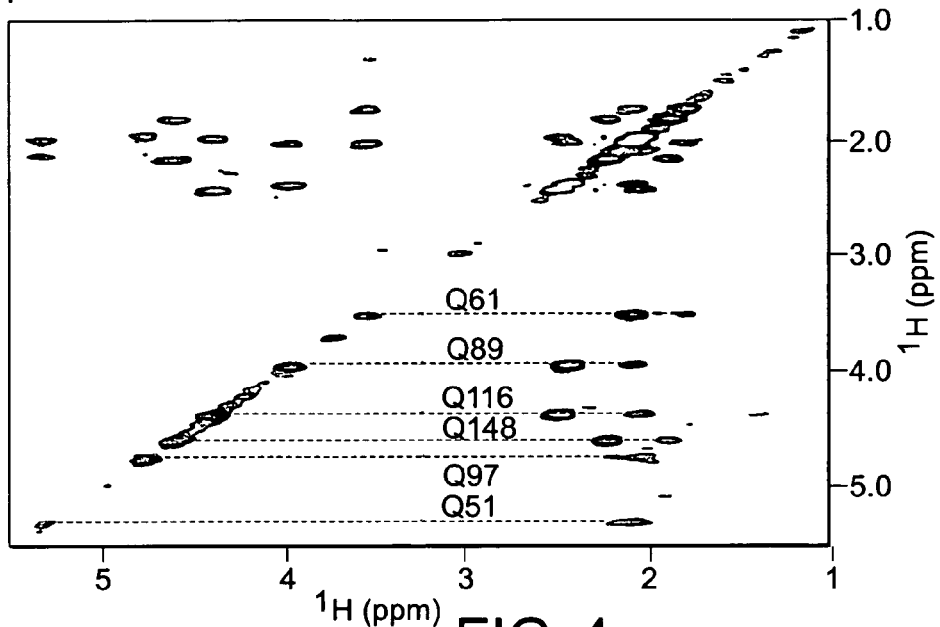
FIG. 4 shows a comparative example of HCCT TOCSY spectra of EPP1b protein (18.2 kDa) containing SAD-glutamine incorporated thereinto.
Figure 4B:
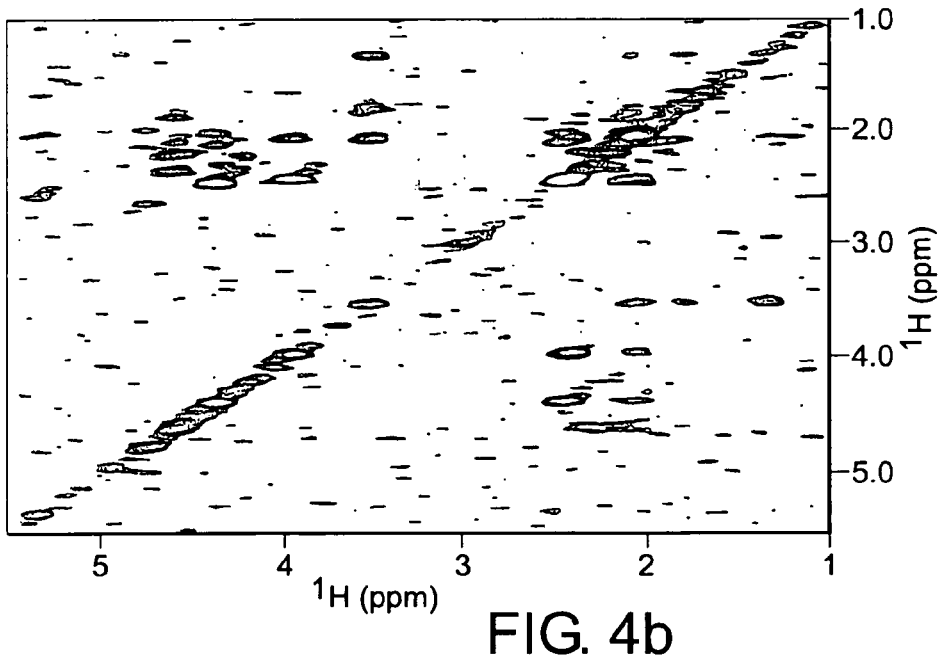

HCCH TOCSY spectra of EPP1b sample containing SAD-glutamine incorporated thereinto were determined. FIG. 4 shows the comparison of the results with those of protein containing [ul-$^{13}$C; $^{15}$N]-glutamine obtained by an ordinary method. It is apparent from FIG. 4 that protein containing SAD-glutamine is more simplified than the protein obtained by the ordinary method. Because the signals of side chains of long-chain amino acids were observed highly sensitively, NMR signals of the side chain of the long-chain amino acids which could not be utilized so far are now utilizable for obtaining the structure information.

Namely, by the technique of the present invention, signals unnecessary for the structure determination disappeared and the sensitivity of the remaining signals is improved. Accordingly, the rapid, reliable signal analysis of a high-molecular weight protein and the determination of the stereostructure thereof with high accuracy are made possible over the range of the prior techniques.

Example 4

Preparation of Protein Containing SAD/PDM-Leucine and NMR Determination Thereof

The synthesis of (2S,3R,4R)-[1,2,3,4,5-$^{13}$C$_5$; 2-$^{15}$N$_2$; 3,5,5,5',5',5'-$^2$H$_6$]leucine (hereinafter referred to as "SAD/PDM-leucine) in steps 18 to 31 will be illustrated according to the following scheme 4:

Scheme 4

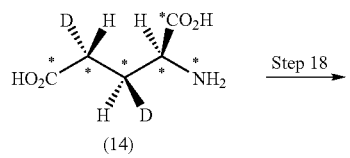
(14)

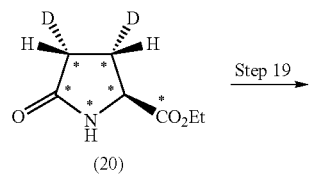
(20)

-continued

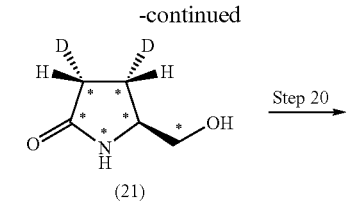
(21)

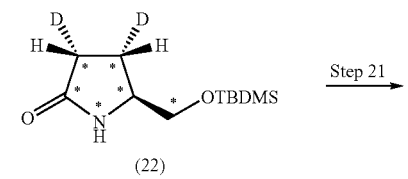
(22)

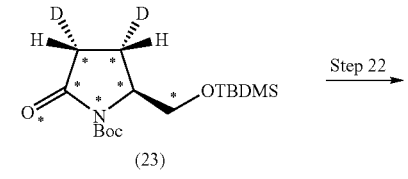
(23)

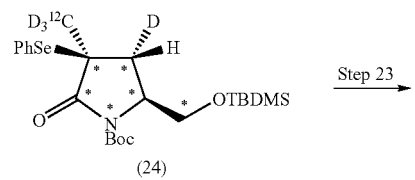
(24)

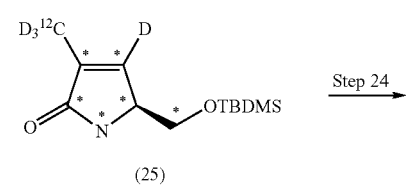
(25)

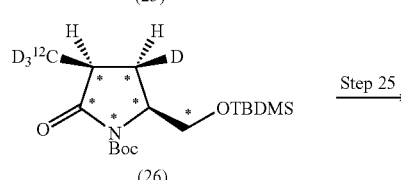
(26)

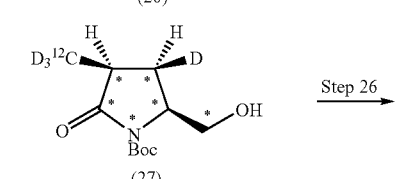
(27)

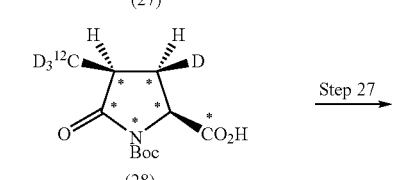
(28)

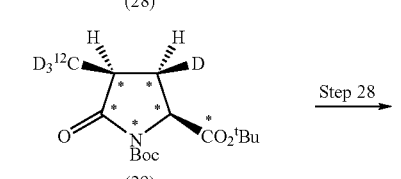
(29)

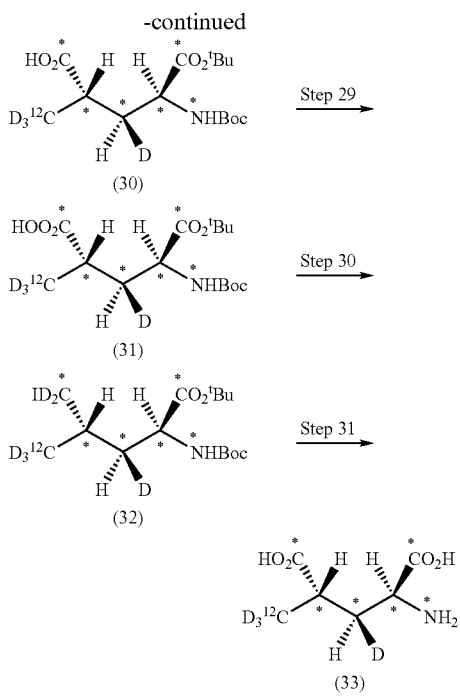

\* = $^{13}C$ or $^{15}N$

<Step 18>

Thionyl chloride (4.52 g, 38.0 mmol) was added dropwise to a solution (20 ml) of SAD-glutamic acid (14) (2.56 g, 16.5 mmol) in ethanol under cooling with ice. The obtained mixture was stirred at room temperature for 1 hour and then refluxed for 1 hour. The solvent was evaporated. $H_2O$ was added to the residue. The reaction mixture was neutralized with saturated sodium hydrogencarbonate and then stirred at 150□ under reduced pressure for 1 hour. The organic matter was extracted with chloroform. The extract was dried over anhydrous magnesium sulfate and then the solvent was evaporated to quantitatively obtain compound (20).

<Step 19>

A suspension (17 ml) of lithium tetrahydroborate (0.40 g, 18.2 mmol) in tetrahydrofuran was added dropwise to a solution (17 ml) of compound (20) (2.73 g, 16.5 mmol) in tetrahydrofuran, and they were stirred at room temperature for 25 hours. 20% acetic acid (20 ml) was added to the reaction mixture, and they were concentrated under reduced pressure. The residue was treated with Dowex 50W-X8 and then concentrated under reduced pressure. The organic matter was extracted with chloroform. The organic layer was dried over anhydrous magnesium sulfate and then concentrated under reduced pressure to obtain compound (21) (1.06 g, 8.65 mmol, 52%).

<Step 20>

Tert-butyldimethylsilyl chloride (1.44 g, 9.52 mmol) and imidazole (1.36 g, 19.9 mmol) were added to a solution (10 ml) of compound (21) (1.06 g, 8.65 mmol) in DMF, and they were stirred at room temperature for 21 hours. The reaction mixture was concentrated under reduced pressure, and the product was extracted from the residue by the extraction with diethyl ether. The organic layer was washed with water and saturated aqueous sodium chloride solution, dried over anhydrous magnesium sulfate and concentrated under reduced pressure to obtain compound (22) (1.69 g, 7.14 mmol, 83%).

<Step 21>

Di-tert-butyl dicarbonate (1.87 g, 8.57 mmol) was added to a solution (15 ml) of compound (22) (1.69 g, 7.14 mmol) in DMF. Then dimethylaminopyridine (0.87 g, 7.14 mmol) was added thereto and they were stirred at room temperature for 22 hours. The reaction mixture was concentrated under reduced pressure, and the product was extracted from the residue with ethyl acetate. The organic layer was washed with an aqueous potassium hydrogensulfate solution and water and then dried over anhydrous magnesium sulfate. The solvent was evaporated and the residue was purified by the silica gel chromatography (developer: hexane/ethyl acetate=85/15) to obtain compound (23) (1.90 g, 5.64 mmol, 79%).

<Step 22>

3,3-Dimethylpropyleneurea (1.45 ml, 11.8 mmol) was added to 1 M hexamethyldisilazane sodium amide/tetrahydrofuran solution (11.8 ml, 11.8 mmol), and they were stirred at 0° C. for 10 minutes. The reaction solution was cooled to −78° C. A solution (10 ml) of compound (23) (1.90 g, 5.64 mmol) in tetrahydrofuran was added thereto and they were stirred at that temperature for 30 minutes. A solution (10 ml) of phenylselenenyl chloride (1.19 g, 6.20 mmol) in tetrahydrofuran was added to the reaction mixture, and they were stirred at −78° C. for 2 hours. Deuterated methyl iodide (0.90 g, 6.20 mmol) was added to the reaction mixture at that temperature. Then the temperature was elevated to room temperature. Ether was added to the reaction mixture. The organic layer was washed with water and saturated aqueous sodium chloride solution and then dried over anhydrous magnesium sulfate. The solvent was evaporated and the residue was purified by the silica gel column chromatography (developer: hexane/ethyl acetate=94/6) to obtain compound (24) (1.52 g, 3.06 mmol, 54%).

<Step 23>

A solution of compound (24) (1.52 g, 3.06 mmol) in tetrahydrofuran (12 ml) was cooled to 0° C., and 30% aqueous hydrogen peroxide solution (3.47 g, 30.6 mmol) was added dropwise thereto. The temperature was elevated to room temperature. After stirring for one hour, the disappearance of the starting material was confirmed by TLC. After the extraction from the reaction mixture with ether, the organic layer was washed with saturated aqueous sodium carbonate solution and dried over anhydrous magnesium sulfate. The solvent was evaporated and the residue was purified by the silica gel column chromatography (developer: hexane/ethyl acetate=85:15) to obtain compound (25) (0.806 g, 2.36 mmol, 77%).

<Step 24>

Platinum dioxide (0.04 g, 5 wt. %) was added to a solution (25 ml) of compound (25) (0.806 g, 2.36 mmol) in methanol, and they were stirred in hydrogen atmosphere for 1 hour. The catalyst was taken by the filtration, and the filtrate was concentrated under reduced pressure to quantitatively obtain compound (26).

<Step 25> p-Toluenesulfonic acid (0.04 g, 0.236 mmol, 10 mol %) was added to a solution (25 ml) of compound (26) (0.81 g, 2.36 mmol) in methanol and they were stirred at room temperature for 18 hours. The reaction mixture was concentrated under reduced pressure. After the extraction with ethyl acetate, the extract was washed with saturated aqueous sodium hydrogencarbonate solution. The organic layer was dried over anhydrous magnesium sulfate and then concentrated under reduced pressure to obtain compound (27) (0.426 g, 1.78 mmol, 75%).

<Step 26>

A mixture of sodium periodate (3.81 g, 17.8 mmol), ruthenium chloride monohydrate (0.11 g) and $H_2O$ (12 ml) was added to a solution (10 ml) of compound (27) (0.426 g, 1.78 mmol) in acetone, and they were stirred at 0° C. for 1 hour. The temperature was elevated to room temperature, and the reaction mixture was stirred for additional 1 hour. The organic layer was separated. Isopropanol (10 ml) was added thereto and they were stirred for 1 hour. The insoluble matter was separated by the filtration. The filtrate was concentrated under reduced pressure and the residue was subjected to the extraction with chloroform. The organic layer was dried over anhydrous magnesium sulfate and the solvent was evaporated to quantitatively obtain compound (28).

<Step 27>

A mixture of N,N-dimethylformamide dineopentylacetal (0.74 g, 3.21 mmol) and tert-butanol (0.40 g, 5.34 mmol) was added to a solution (10 ml) of compound (28) (0.45 g, 1.78 mmol) in benzene under reflux, and they were refluxed for additional 30 minutes. The reaction solution was cooled to room temperature. Ethyl acetate was added thereto. The organic layer was washed with water, saturated aqueous sodium hydrogencarbonate solution and saturated aqueous sodium chloride solution and then dried over anhydrous magnesium sulfate. The solvent was evaporated, and the residue was purified by the silica gel column chromatography (developer: hexane/ethyl acetate=80:20) to obtain compound (29) (0.271 g, 0.88 mmol, 49%).

<Step 28>

A solution of compound (29) (0.271 g, 0.88 mmol) in tetrahydrofuran (10 ml) was cooled to 0° C. 1 M aqueous LiOH solution (1.05 ml) was added dropwise to the solution. The temperature of the reaction mixture was elevated to room temperature. After stirring for 30 minutes, the disappearance of the starting material was confirmed by TLC. The product was extracted with saturated aqueous sodium hydrogencarbonate solution and then washed with ethyl acetate. pH of the aqueous layer was adjusted to 3 to 4 with citric acid. The organic product was extracted with ethyl acetate. The organic layer was dried over anhydrous magnesium sulfate and then the solvent was evaporated to quantitatively obtain compound (30).

<Step 29>

A solution (10 ml) of compound (30) (0.287 g, 0.88 mmol) in tetrahydrofuran was cooled to −40° C. in argon gas stream. Triethylamine (0.12 g, 1.14 mmol) and isobutyl chloroformate (0.15 g, 1.05 mmol) were added to the solution, and they were stirred for 1 hour. Triethylamine hydrochloride thus precipitated was removed by the filtration in argon stream. The filtrate was cooled to 0° C. and a mixture of sodium boron deuteride (0.11 g, 2.63 mmol), tetrahydrofuran (8 ml) and deuterium oxide (6 ml) was added thereto. The obtained mixture was stirred for 1.5 hours. The reaction mixture was diluted with ethyl acetate and then washed with saturated aqueous sodium chloride solution, 10% aqueous citric acid solution and saturated aqueous sodium chloride solution. The organic layer was dried over anhydrous magnesium sulfate. The solvent was evaporated, and the residue was purified by the silica gel column chromatography (developer: hexane/ethyl acetate=75:25) to obtain compound (31) (0.168 g, 0.53 mmol, 61%).

<Step 30>

Iodine (0.30 g, 1.17 mmol) was added to a suspension (5 ml) of triphenylphosphine (polystyrene-supported 3 mmol P/g resin, 0.39 g, 1.17 mmol) in dichloromethane, and they were stirred at room temperature for 10 minutes. Then imidazole (0.08 g, 1.17 mmol) was added to the obtained mixture, and they were stirred at room temperature for 10 minutes. A solution (15 ml) of compound (31) (0.168 g, 0.533 mmol) in dichloromethane was added to the reaction mixture, and they were refluxed for 2 hours. The insoluble matter was removed by the filtration and the filtrate was concentrated under reduced pressure. The product was extracted from the residue with ether and then washed with saturated sodium thiosulfate solution. The organic layer was dried over anhydrous magnesium sulfate and concentrated under reduced pressure to obtain compound (32) (0.199 g, 0.468 mmol, 88%).

<Step 31>

Tributyltin hydride (0.21 g, 0.70 mmol) and azobisisobutyronitrile (AIBN) (7.7 mg) were added to a solution (10 ml) of compound (32) (0.199 g, 0.468 mmol) in benzene, and they were stirred for 1 hour. The solvent was evaporated. 1 M hydrochloric acid (15 ml) was added to the residue, and they were refluxed at 130° C. for 1 hour. The aqueous layer was washed with chloroform and then concentrated under reduced pressure. After the ion exchange with Dowex 50W-X8, SAD/PDM-leucine (33) (0.0486 g, 0.34 mmol, 73%) was obtained.

<Preparation of Labeled Protein>

A protein sample containing the above-described SAD/PDM-leucine incorporated thereinto was prepared by adding SAD/PDM-leucine to EPP1b protein as the model protein under conditions described in a thesis (E. Kariya et al., J. Biomol. NMR 18, 75–76, 2000).

<Example of NMR Determination of Labeled Protein>

An NMR sample was assigned according to information of the assignment of protein main chain NMR signals described in a thesis (E. Kariya et al., J. Biomol. NMR 18, 75–76, 2000) under conditions described in the same thesis.

Figure 5A:
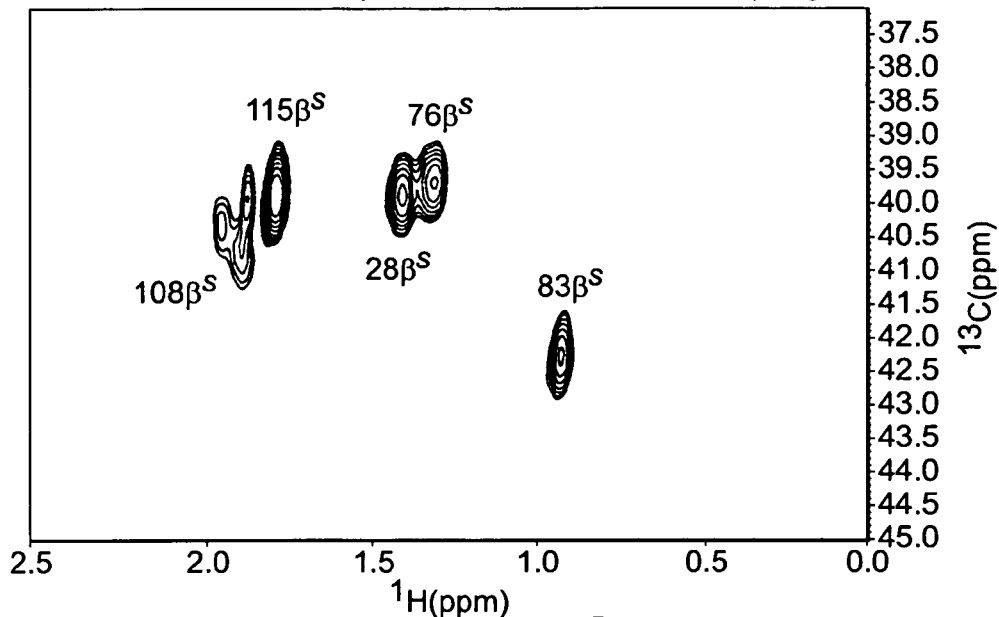
FIG. 5 shows a comparative example of $^1H$-$^{13}C$ HSQC spectra in $^1H$-$^{13}C$ β region of EPP1b protein (18.2 kDa) containing SAD/PDM-leucine incorporated thereinto.
Figure 5B:
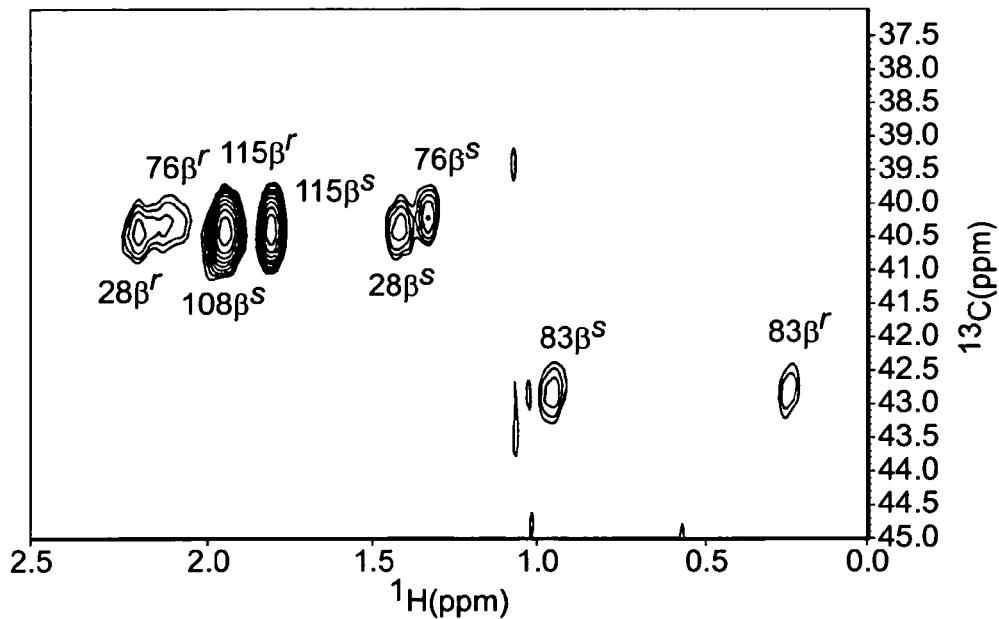
Figure 6A:
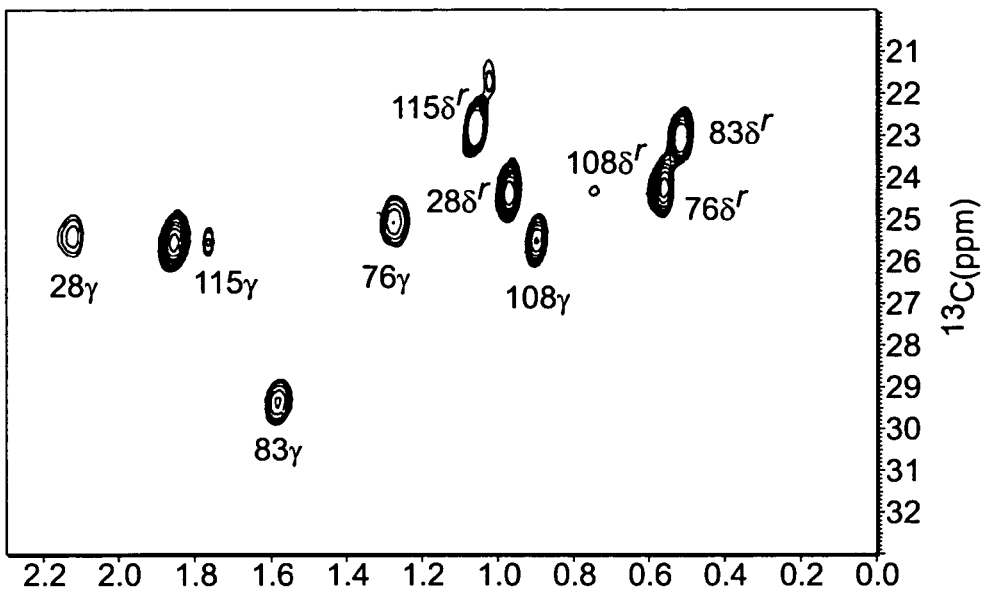
FIG. 6 shows a comparative example of $^1H$-$^{13}C$ HSQC spectra in $^1H$-$^{13}C$γ region of EPP1b protein (18.2 kDa) containing SAD/PDM-leucine incorporated thereinto.
Figure 6B:
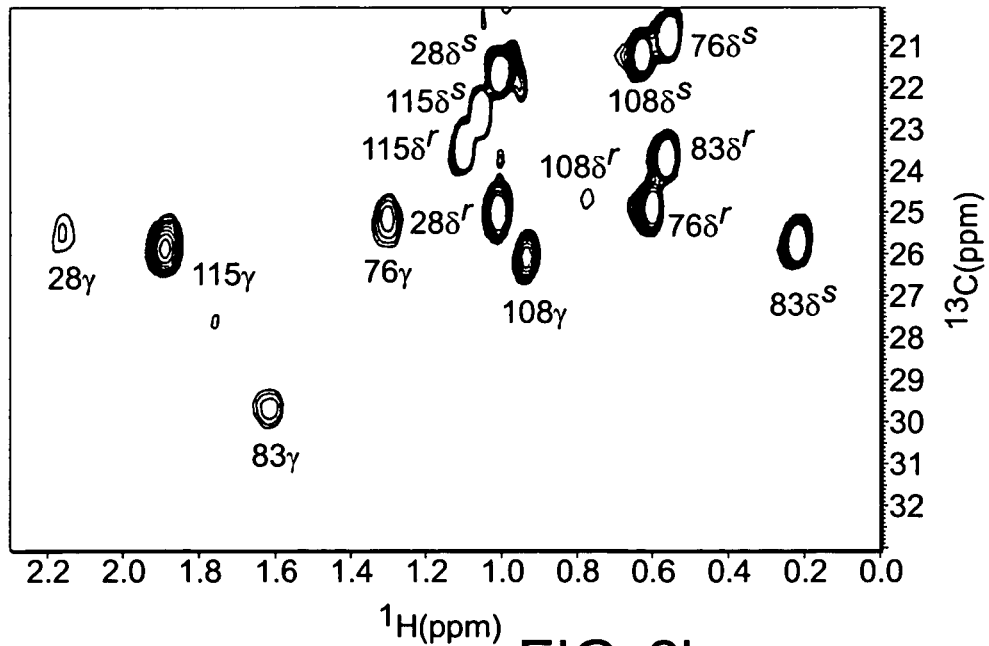

$^1$H-$^{13}$CCT-HSQC of EPP1b sample containing SAD/PDM-leucine incorporated thereinto was determined. FIGS. 5 and 6 show the comparison of the results with those of protein containing [ul-$^{13}$C; $^{15}$N]-leucine obtained by an ordinary method. It is apparent from FIGS. 5 and 6 that signals of protein containing SAD/PDM-leucine is more simplified than those of the protein obtained by the ordinary method. It is to be noted that one of methyl groups in leucine was completely deuterated and carbon atom was kept as nuclear spin-free $^{12}$C, while in the other methyl group, two of the three hydrogen atoms are deuterated and the remaining hydrogen atom, which was the minimum necessary hydrogen atom, was kept for obtaining the structure. The central carbon atom is replaced with $^{13}$C for the NMR determination and assignment. The line width is reduced as the proton density is lowered to almost completely compensate for the reduction in number of protons in the deuteration. In the complicated measurement method for the actual structure determination, the determination sensitivity is expected to be rather remarkably improved as compared with that of ordinary methods.

Thus, when SAD/PDM-amino acids are used, all carbon atoms having proton are only $^{13}$C-$^1$H. Thus, it is made possible to obtain labeled protein samples indispensable for the development of new NMR techniques such as the determination and analysis of the relaxation time and the application of the residual dipole interaction constant to the structure determination.

Example 5

Preparation of Protein Containing SAD/PDM-Methionine Incorporated thereinto and NMR Determination Steps 32 to 38 illustrate the synthesis of (2S,3R,4R)-[1, 2,3,4,6-$^{13}$C$_5$;2-$^{15}$N;3,4,6, 6-2H$_4$]methionine (hereinafter referred to as SAD/PDM-methionine) according to the following scheme 5:

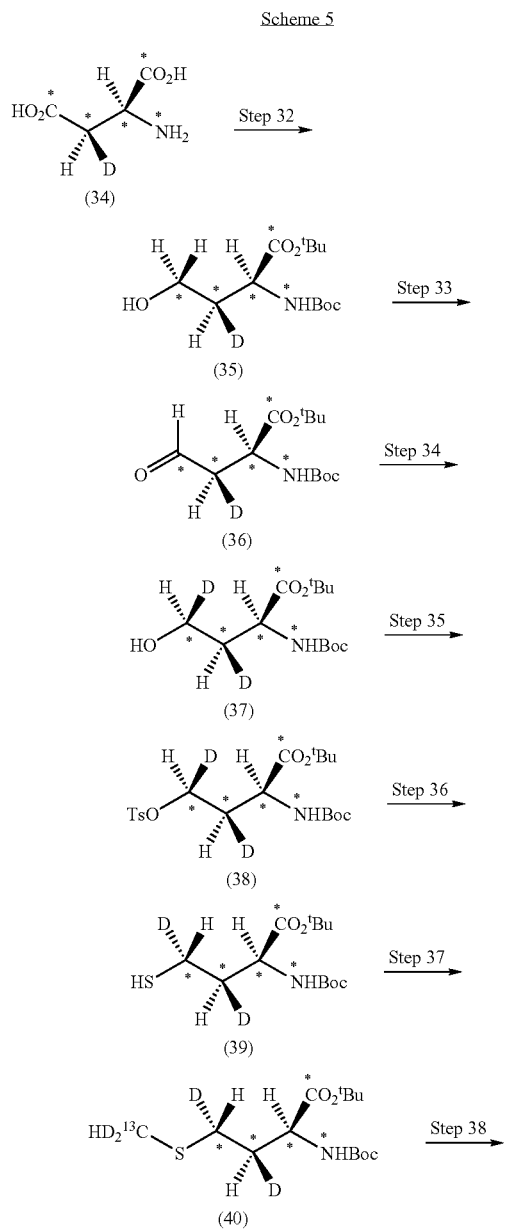

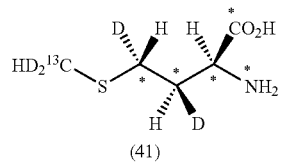

(41)

<Steps 32 and 33>

(2S,3R)-[1,2,3,4-$^{13}$C$_4$;2-$^{15}$N;3-$^2$H] aspartic acid (34) was converted into compound (35) with reference to a method disclosed in a literature (K. Ramalingam et al., J. Org. Chem. 53, 1900–1903, 1988). Compound (35) (2.82 g, 10 mmol) was dissolved in dichloromethane (10.0 ml). The obtained solution was added dropwise to a solution of Dess-Martin-periodinane (4.84 g, 11.4 mmol) in methylene chloride (30.0 ml) during 20 minutes. After stirring for 1 hour, diethyl ether (50 ml) was added to the obtained mixture and then a mixture of saturated sodium hydrogencarbonate (50.0 ml) and sodium thiosulfate (15.0 g) was added thereto, and they were stirred for 10 minutes. The organic layer was washed with saturated sodium hydrogencarbonate (50.0 ml) and water (50.0 ml) and then dried over magnesium sulfate. The solvent was evaporated, and the obtained crude product was purified by the silica gel column chromatography (developer: hexane/ethyl acetate=1/1) to quantitatively obtain compound (36).

<Step 34>

A mixture of ethanol (60.6 ml, 2.78 g) and tetrahydrofuran (16.0 ml) and then a solution of (s)-(-)-1,1'-bi-2-naphtol (60.6 mmol, 17.34 g) in tetrahydrofuran (90.0 ml) were slowly added to a mixture of lithium aluminum hydride (60.0 mmol, 2.28 g) and tetrahydrofuran (4.0 ml) with a syringe under stirring in nitrogen atmosphere. The obtained mixture was stirred at room temperature for 30 minutes. The reaction mixture was cooled to −100° C. A solution of compound (36) (1.67 g, 6.00 mmol) in tetrahydrofuran (11.0 ml) was slowly added to the reaction mixture with a syringe, and they were stirred at that temperature for 3 hours. Then the reaction mixture was stirred at −78° C. for 10 hours. 0.5 N hydrochloric acid (1.0 ml) was added thereto, and they were stirred for 15 minutes. The reaction mixture was filtered through Hyflo Super Cel. The organic layer was dried over magnesium sulfate, and the solvent was evaporated. Hexane was added to the obtained crude product. Excess naphthol was removed by the crystallization. The product was purified by the silica gel column chromatography (developer: hexane/ethyl acetate=1:1) to obtain compound (37). (0.315 g, 1.12 mmol, 19%)

<Step 35>

Compound (37) (0.315 g, 1.12 mmol) was dissolved in methylene chloride (15.0 ml). Triethylamine (0.125 g, 1.23 mmol) was added to the obtained solution in nitrogen stream at 0° C. Then methanesulfonyl chloride (0.141 g, 1.23 mmol) was added to the mixture and they were stirred for 1 hour. Water (10.0 ml) was added thereto and they were stirred for 15 minutes. The organic layer was washed with 0.5 N hydrogen chloride (30 ml×2), water (30 ml×2), saturated sodium hydrogencarbonate (30 ml×2) and saturated aqueous sodium chloride solution (30 ml×2) and then dried over magnesium sulfate. The solvent was evaporated.

The obtained crude product was purified by the silica gel column chromatography (developer: hexane/ethyl acetate=1/1) to obtain compound (38) (0.360 g, 1.10 mmol, 98%).

<Step 36>

Water (20 ml), potassium O-t-butyl dithiocarbonate (0.225 g, 1.21 g) and Aliquat 336 (33.0 mg, 37.0 μl) were added to compound (38) (0.360 g, 1.10 mmol), and they were strongly stirred at room temperature for 30 minutes. Then the mixture was stirred at 45 to 50° C. for 10 minutes. The temperature was elevated to a range of 75 to 80° C. during at least 10 minutes and then the mixture was stirred for 20 minutes. After the aqueous layer became transparent and yellow oily product was formed, petroleum ether (20.0 ml) was added to the reaction mixture. The organic layer was washed with water (30.0 ml×2) and then dried over magnesium sulfate. The obtained crude product was purified by the silica gel column chromatography (developer: hexane/ethyl acetate=1/1) to obtain compound (39). (0.101 g, 0.340 mmol, 31%).

<Step 37>

Compound (39) (0.101 g, 0.340 mmol) was dissolved in tetrahydrofuran (15.0 ml) in nitrogen stream. 1.6 M n-butyl lithium (0.233 ml) was added to the obtained solution at −78° C. and they were stirred for 15 minutes. $^{13}CD_2HI$ (54.2 mg, 0.374 mmol) was added to the obtained mixture, and they were stirred for 90 minutes. Saturated ammonium chloride solution (1.00 ml) was added to the reaction mixture and they were stirred for 5 minutes. The temperature was elevated to room temperature. After evaporating THF, ethyl acetate (30.0 ml) was added to the residue. The organic layer was washed with water (30.0 ml) and saturated aqueous sodium chloride solution (30.0 ml) and then dried over magnesium sulfate. The solvent was evaporated, and the obtained crude product was purified by the silica gel column chromatography (developer: hexane/ethyl acetate=1/1) to obtain compound (40). (99.3 mg, 0.317 mmol, 93%).

<Step 38>

1 N hydrochloric acid (15 ml) was added to compound (40) (99.3 mg, 31.7 mmol), and they were refluxed at 110° C. for 3 hours. Water was evaporated. The obtained hydrochloride was dissolved in a small amount of water and then purified with ion exchange resin Dowex 50W-X8 to almost quantitatively obtain SAD/PDM-methionine (41) (50.1 mg, 0.320 mg, >99%).

<Preparation of Labeled Protein>

A protein sample containing the above-described SAD/PDM-methionine incorporated thereinto was prepared by adding SAD/PDM-methionine to EPP1b protein as the model protein under conditions described in a thesis (E. Kariya et al., J. Biomol. NMR 18, 75–76, 2000).

<Example of NMR Determination of Labeled Protein>

An NMR sample was assigned according to an information of the assignment of protein main chain NMR signals described in a thesis (E. Kariya et al., J. Biomol. NMR 18, 75–76, 2000) under conditions described in the same thesis.

Figure 7A:
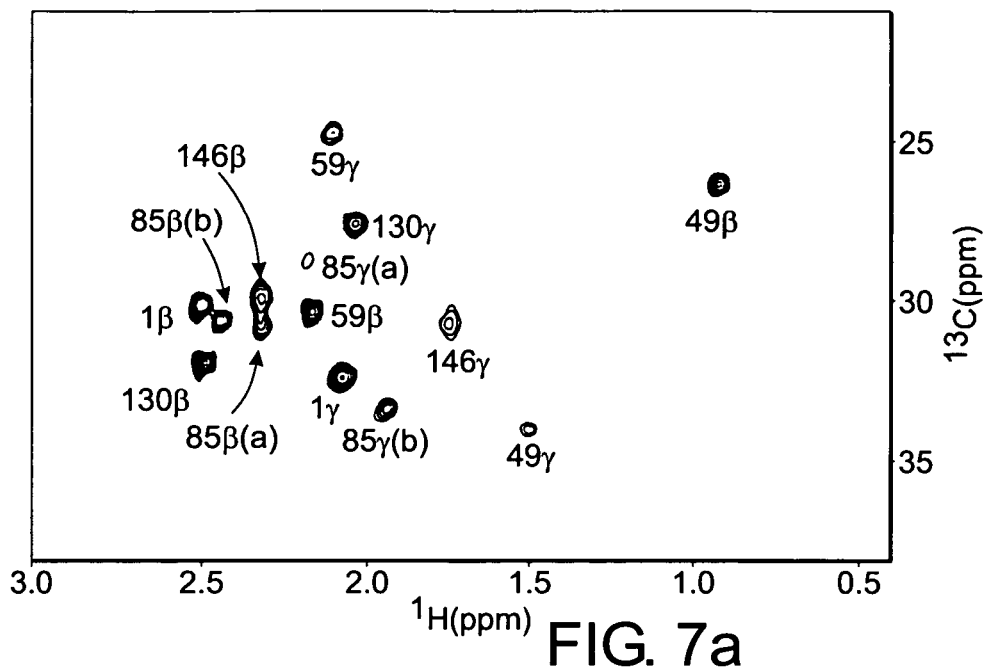
FIG. 7 shows a comparative example of $^1H$-$^{13}C$ HSQC spectra in $^1H$-$^{13}C$ γ region of EPP1b protein (18.2 kDa) containing SAD/PDM-methionine incorporated thereinto.
Figure 7B:
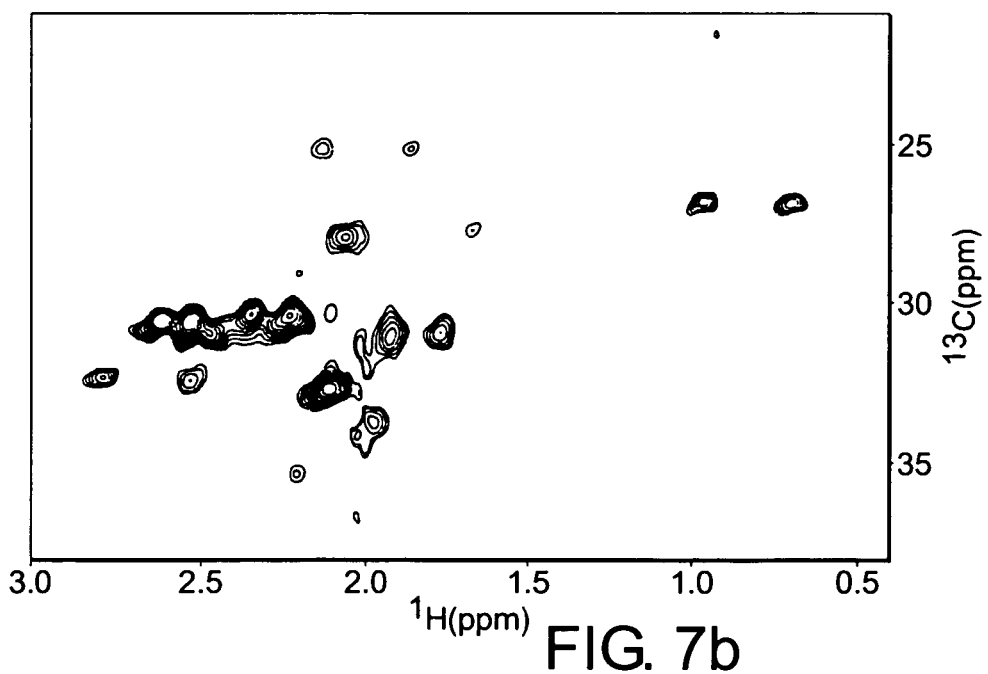
Figure 8A:
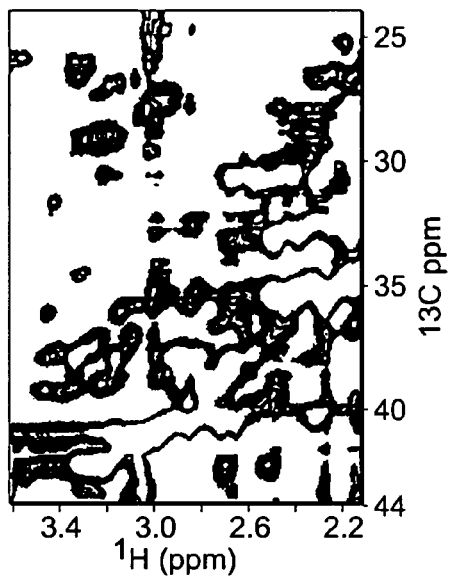
FIG. 8 shows a comparative example of $^1H$-$^{13}C$ HSQC spectra in $^1H$-$^{13}C$βregion of EPP1b protein (18.2 kDa) containing an aromatic amino acid SSD-labeled at the β-position.
Figure 8B:
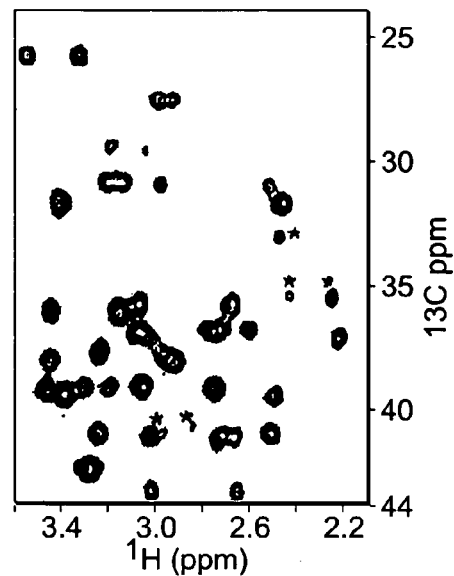
Figure 8C:
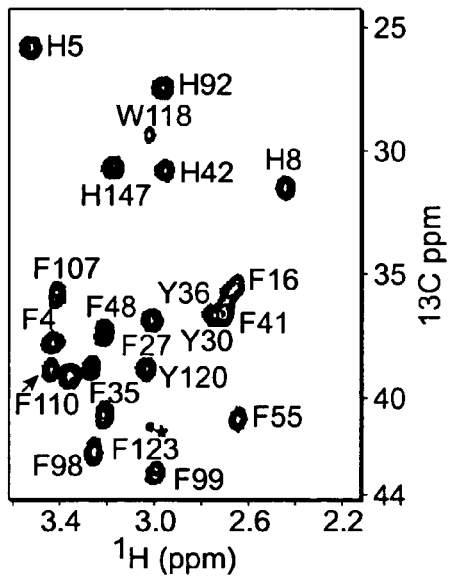
Figure 8D:
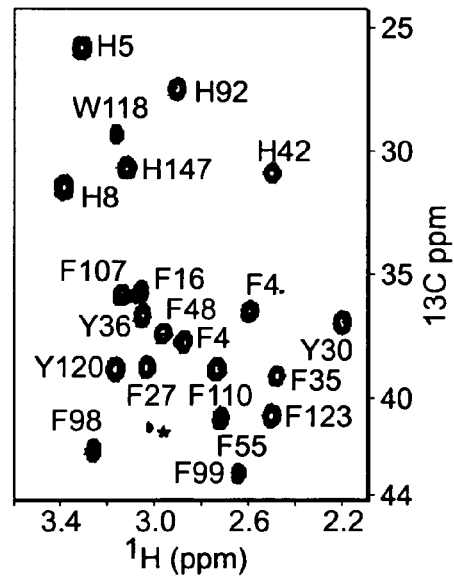

$^1H$-$^{13}C$ CT-HSQC of EPP1b sample containing SAD/PDM-methionine incorporated thereinto was determined. FIG. 7 shows the comparison of the results with those of protein containing [ul-$^{13}C$; $^{15}N$]-methionine obtained by an ordinary method. It is apparent from FIG. 7 that protein containing SAD/PDM-methionine is more simplified than the protein obtained by the ordinary method. Because the signals of side chains of long-chain amino acids could be observed highly sensitively, NMR signals of the side chain of the long-chain amino acids which could not be utilized so far are now utilizable for obtaining the structure information.

Namely, by the technique of the present invention, signals unnecessary for the structure determination disappeared and the sensitivity of the remaining signals is improved. Accordingly, the rapid, reliable signal analysis of a high-molecular weight protein and the determination of the stereostructure thereof with high accuracy are made possible over the range of the prior techniques.

Example 6

Preparation of Protein Containing Aromatic Amino Acids Labeled with SSD at the I-Position and NMR Determination Synthesis of (2S,3R) and (2S,3S)-[3,2',3',4',5',6'-$^2H_6$; 1,3-$^{13}C_2$; 2-$^{15}N$]-phenylalanine, tyrosine, tryptophan and histidine:

They were synthesized with reference to a method described in a literature (Makoto Oba et al., J. Chem. Soc., Perkin Trans. 1, 1995, 1603).

<Preparation of Labeled Protein>

A protein sample containing the above-described stereoselectively deuterium-labeled aromatic acid was prepared by using EPP1b protein as the model protein under conditions described in a thesis (E. Karia et al., J. Biomol. NMR 18, 75–76, 2000).

<Example of NMR Determination of Labeled Protein>

An NMR sample was assigned according to information of the assignment of protein main chain NMR signals described in a thesis (E. Kariya et al., J. Biomol. NMR 18, 75–76, 2000) under conditions described in the same thesis.

$^1H$-$^{13}C$ HSQC of EPP1b sample containing labeled aromatic amino acids incorporated thereinto was determined. FIG. 8 shows the comparison of the results with those obtained by an ordinary method. It is apparent from FIG. 8 that NMR spectra of protein containing SSD-labeled amino acids are simplified (c and d), while NMR spectra of protein obtained by the ordinary method are not simple (a and b). The assignment of stereospecific signals without error is also possible.

Figures 9A, 9B, 9C, 9D:
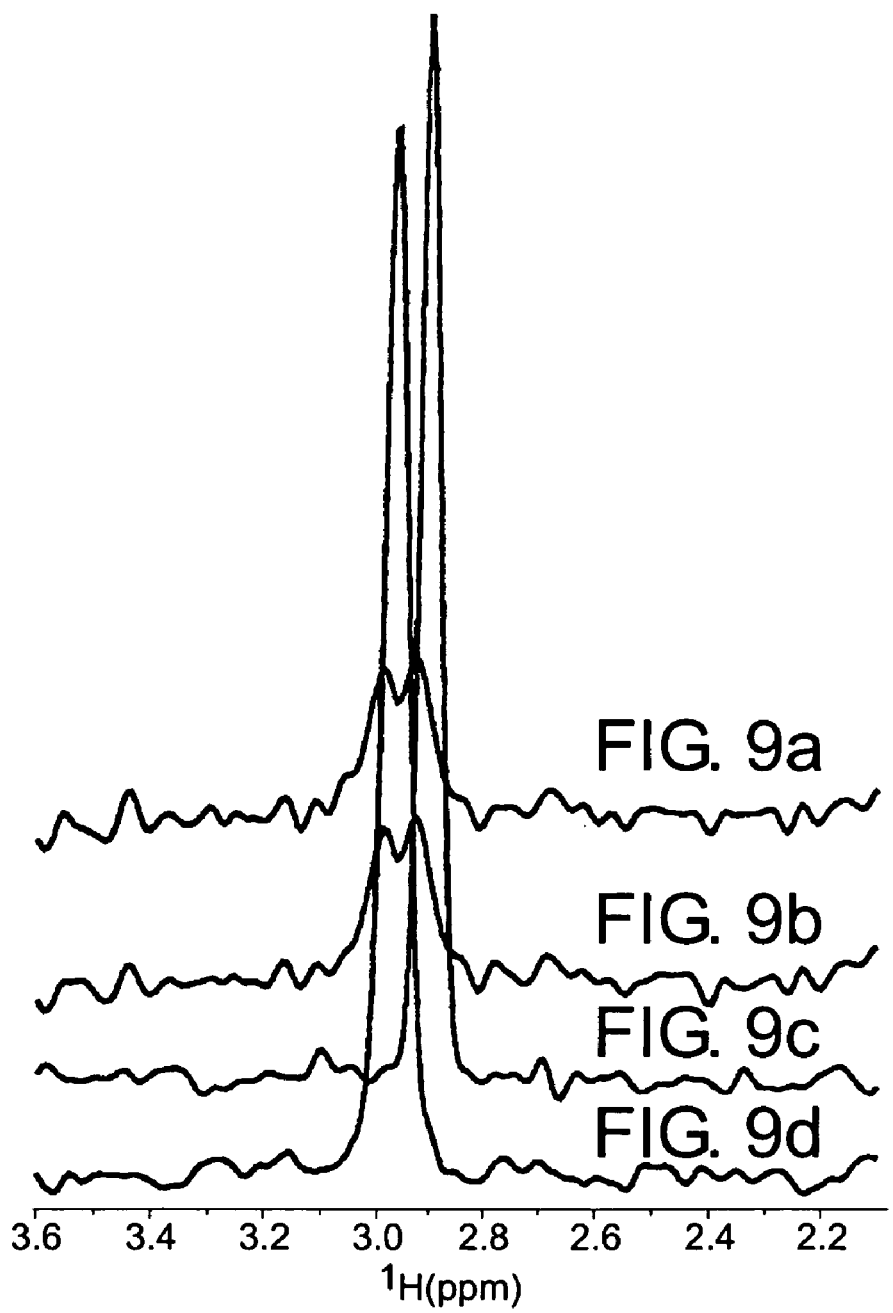
FIG. 9 shows a comparative example of slice data of H 92 signals.

Slice data of His 92 signals are shown in FIG. 9. As shown in FIG. 9, the signal strength of SSD-labeled histidine is about 7 times as high as that of non-deuterated histidine residue because the former is free from the CH, HH dipole interaction.

Namely, by the technique of the present invention, signals unnecessary for the structure determination disappeared and the sensitivity of the remaining signals is improved. Accordingly, the rapid, reliable signal analysis of a high molecular weight protein and the determination of the stereostructure with high accuracy are made possible over the range of the prior techniques.

Example 7

Preparation of Protein Comprising only Stable Isotope-Labeled Amino Acids (Hereinafter Referred to as SAIL Amino Acids), NMR Determination and Structure Analysis SAIL amino acids other than those synthesized in the above-described Examples, i.e. SAIL alanine, SAIL valine, SAIL isoleucine, SAIL serine, SAIL proline and SAIL arginine, were synthesized by methods described below.

Synthesis of SAIL Alanine:

This compound was synthesized by the Schiff base alkylation of methyl ester of [1,2-$^{13}C_2$; 2-$^{15}$N]glycine with benzophenonimine. The structural formula of synthesized SAIL alanine is shown in FIG. 1.

Synthesis of SAIL Valine:

SAIL valine was synthesized by partially changing a method described in a literature (Jack E. Baldwin et al., Tetrahedron, 51, 4089–4100 (1995)) so as to obtain the intended labeled pattern (scheme 6). Namely, [1,2,3,4-$^{13}C_4$; 2-$^{15}$N]aspartic acid was used as the substrate, [$^2H_3$]methyl iodide was used as the methylating agent in step 39 and NaBD$_4$/MeOD was used for realizing the reduction conditions in Step 40.

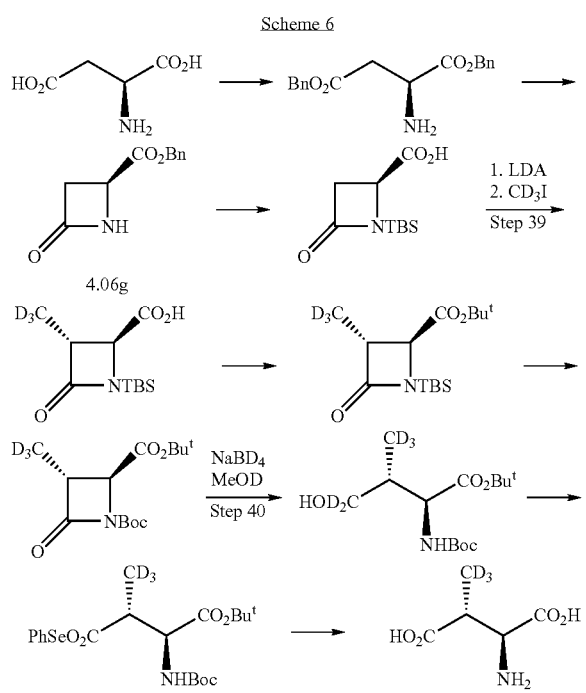

Scheme 6

Synthesis of SAIL Proline:

SAIL proline was derived from uniformly $^{13}$C,$^{15}$N-labeled L-glutamic acid by a method described in a literature (M. Oba et al., J. Org. Chem. 64, 9275–9278, 1999). The structural formula of synthesized SAIL proline is shown in FIG. 1.

Synthesis of SAIL Arginine:

SAIL arginine was synthesized according to scheme 7. Steps 41 to 43 will be illustrated in detail below.

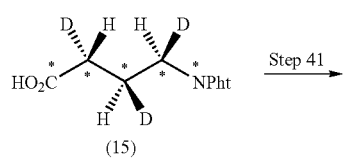

Scheme 7

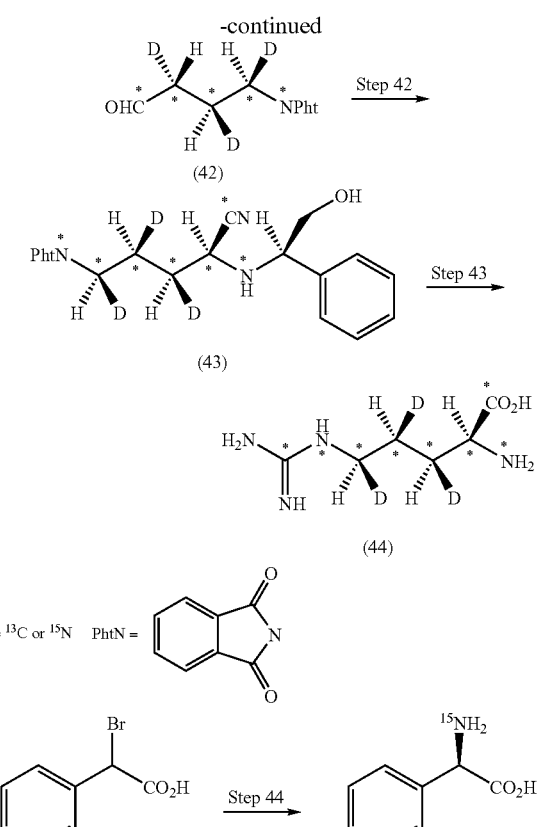

\* = $^{13}$C or $^{15}$N  PhtN =

<Step 41>

Compound (15) (2.41 g, 10 mmol) obtained in step 13 was dissolved in methylene chloride (20 ml). Thionyl chloride (11.9 g, 100 mmol) was added to the obtained solution at room temperature. The obtained solution was stirred at room temperature for 1 hour and then at 40° C. for 2 hours. The reaction solution was concentrated under reduced pressure. The obtained residue was dissolved in benzene. Tetrakistriphenylphosphine palladium (0.21 g, 5 w/w %) and tributyltin deuteride (3.227 ml, 12 mmol) were added thereto in argon atmosphere and they were stirred at room temperature for 5 minutes. The reaction mixture was concentrated. The product was purified by the silica gel column chromatography with hexane/ethyl acetate=7/3 to obtain compound (42) (2.101 g, 9.34 mmol, 93%).

<Step 42>

(2R)-[2-$^{15}$N]-Phenyoglycinol (0.44 g, 3.2 mmol) was added to a solution (32 ml) of compound 42 (0.721 g, 3.2 mmol) in methylene chloride, and they were stirred at room temperature in nitrogen atmosphere for 1 hour. [$^{13}$C]-sodium cyanide (0.32 g, 6.4 mmol) and acetic acid (0.387 ml, 6.4 mmol) were successively added to the reaction mixture, and they were stirred at room temperature for 24 hours. 6 M hydrochloric acid (10 ml) was added to the reaction mixture. After the extraction with chloroform the organic layer was dried over anhydrous magnesium sulfate and then concentrated under reduced pressure. The residue was purified by the flash silica gel column chromatography with hexane/ethyl acetate to obtain compound 43 (0.7624 g, 2.044 mmol, 64%).

<Step 43>

Compound 43 (0.7624 g, 2.044 mmol) obtained in step 42 was dissolved in a solution of methanol/chloroform=1/2 and the obtained solution was cooled to 0° C. Palladium acetate (1.55 g, 3.17 mmol) was added thereto and they were stirred for 5 minutes. 0.2 M phosphate buffer (50 ml) was added to the reaction solution and they were stirred at 0° C. for 40 minutes. Crystals thus formed were taken by the filtration, and the filtrate was subjected to the extraction with chloroform. The chloroform layer was dried over anhydrous magnesium sulfate and then concentrated under reduced pressure. Concentrated hydrochloric acid (50 ml) was added to the residue and they were stirred in an oil bath at 140° C. for 5 hours. The reaction solution was concentrated and then ion-exchanged with Dowex 50W-X8 to obtain ornithine (0.583 g). Ornithine thus obtained was dissolved in water (3 ml). Basic copper carbonate (1.62 g, 7.32 mmol) was added to the obtained solution, and they were stirred at 80° C. for 24 hours. Insoluble crystals were filtered out, and the filtrate was concentrated by the freeze-drying. The obtained solid was dissolved in water (1.8 ml), and the obtained solution was cooled to 0° C. O-methylisourea hydrochloride (0.246 g, 2.116 mmol) and then 7.4% aqueous sodium hydroxide solution (1.15 ml, 2.116 mmol) were added to the solution. The temperature of the obtained mixture was elevated to room temperature, and the mixture was stirred for 5 days. The reaction solution was purified with Dowex 50W-X8. Hydrochloric acid was added to arginine thus obtained to adjust pH thereof to 6. After freeze-drying, arginine hydrochloride (0.394 g, 1.765 mmol) was obtained.

<Step 44>

Synthesis of (2R)-[2-$^{15}$N]phenylglycinol

A magnetic stirrer, a-bromophenylacetic acid (4.3 g, 20 mmol) and methanol (20 ml) were fed into a 50 ml autoclave tube, and they were cooled with an ice bath. Ammonia gas was introduced therein until the saturation, the tube was tightly sealed and the temperature was elevated to room temperature. After stirring for 24 hours, crystals formed in the reaction system were taken by the filtration and then dried to obtain (2SR)-[2-$^{15}$N]phenylglycine (2.733 g, 17.98 mmol). (2SR)-[2-$^{15}$N]Phenylglycine thus obtained was converted into (2R)-[2-$^{15}$N]phenylglycine by a method descried in a literature (T. Shiraiwa et al., Bull. Chem. Soc. Jpn., 64, 191–195, 1991). The yield was 1.90 g (12.498 mmol). Obtained (2R)-[2-$^{15}$N]phenylglycine was converted to (2R)-[2-$^{15}$N]phenylglycinol by a method described in a literature (Ernesto Nicols et all., J. Org. Chem., 58, 766–770, 1993). The yield was (10.125 mmol).

Synthesis of SAIL Isoleucine:

SAIL Isoleucine was synthesized according to the following scheme 8 and scheme 9 with reference to literatures shown below:

Scheme 8

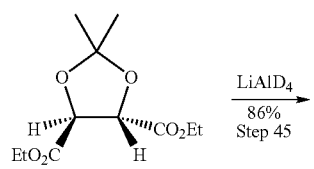

-continued

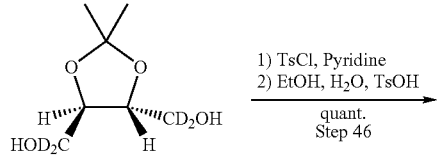

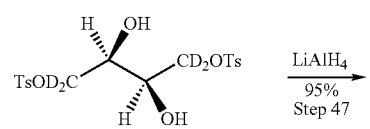

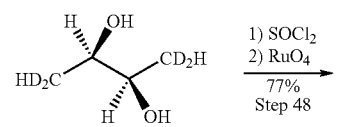

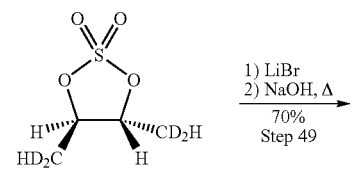

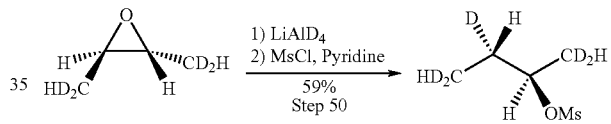

Scheme 9

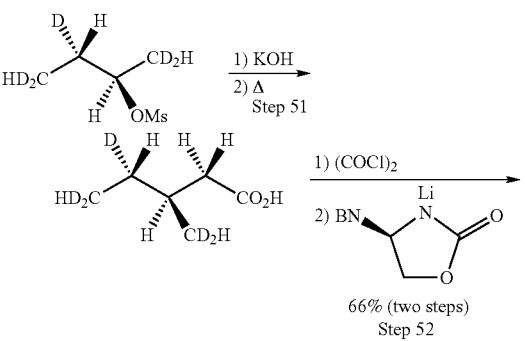

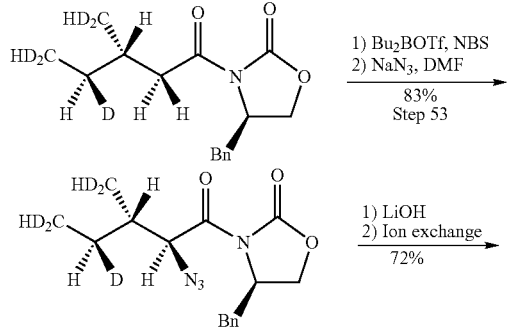

| Diastereomer | Yield |
|---|---|
| S | 83 |
| R | 7 |

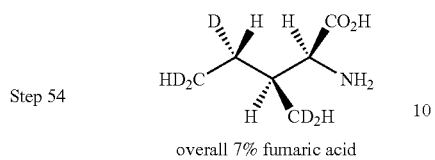

Step 54 overall 7% fumaric acid

<Step 45, Step 46>

[1,2,3,4-$^{13}C_4$; 1,1,4,4-$^2H_4$]2,3-butanediol was synthesized from a $^{13}C$ uniformly labeled tartaric acid derivative by a method described in a literature (V. Schurig et al., J. Org. Chem., 45, 538–541, 1980).

<Steps 47 to 51>

Butanediol obtained in step 46 was converted into isobutyric acid by a method described in a literature (Richard K. Hill et al., J. Am. Chem. Soc., 102, 7344–7348, 1980).

<Steps 51 to 54>

Isobutyric acid obtained in Step 51 was converted into SAIL isoleucine by a method described in a literature (Nicholas M. Kelly et al., Tetrahedron Let., 37, 1517–1520, 1996).

Synthesis of SAIL Threonine:

SAIL threonine was synthesized according to scheme 10 with reference to literatures shown below:

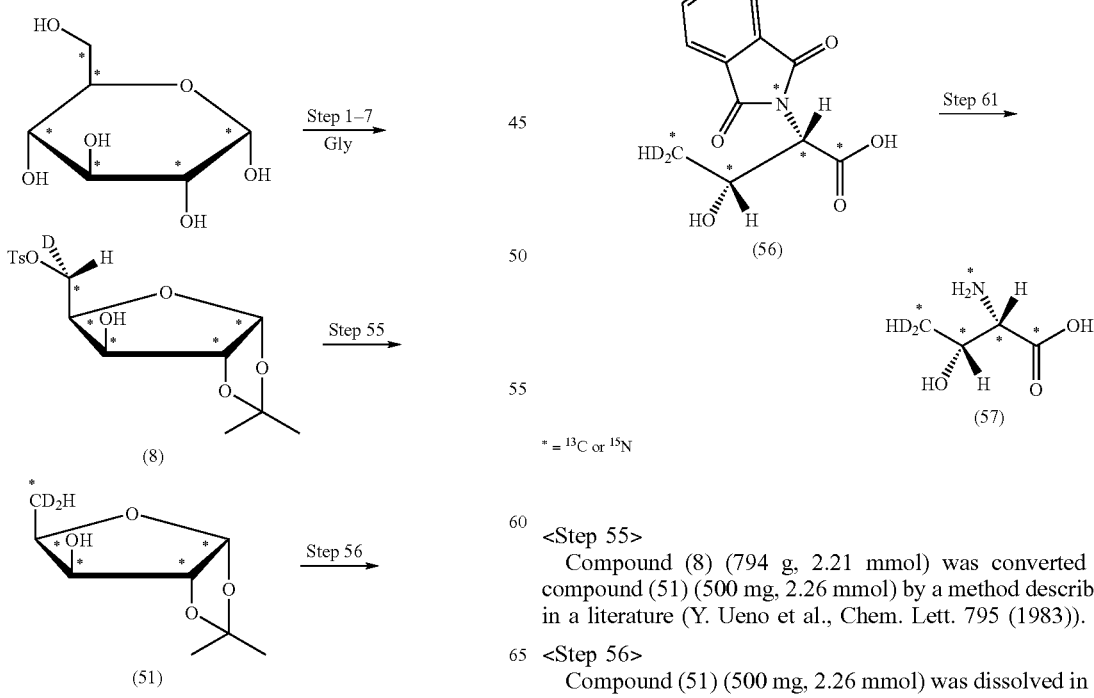

\* = $^{13}C$ or $^{15}N$

<Step 55>

Compound (8) (794 g, 2.21 mmol) was converted to compound (51) (500 mg, 2.26 mmol) by a method described in a literature (Y. Ueno et al., Chem. Lett. 795 (1983)).

<Step 56>

Compound (51) (500 mg, 2.26 mmol) was dissolved in 30 ml of methine chloride. The temperature was lowered to 0°

C. Dess-Martin reagent (1.90 g, 4.49 mmol) was added to the solution, and they were stirred while the temperature was kept at 0° C. The temperature was elevated to room temperature, and the reaction mixture was stirred for 1.5 hours. 60 ml of saturated sodium hydrogencarbonate containing 12 g of sodium thiosulfate dissolved therein and 50 ml of ethyl acetate were added to the reaction mixture, and they were stirred for 5 minutes. After washing with 50 ml of saturated sodium hydrogencarbonate solution twice, with 50 ml of water once and with 50 ml of brine once, the organic layer was dried over sodium sulfate and then concentrated under reduced pressure to obtain compound (52).

<Step 57>

Compound (52) was dissolved in 20 ml of methanol. The obtained solution was cooled to 0° C. A solution of sodium borohydride (70 mg, 1.75 mmol) in 10 ml of methanol was added thereto. 2 minutes after, the obtained mixture was taken out of the ice bath and stirred for 1.5 hours. 10 ml of acetone was added thereto and they were stirred for 5 minutes. 20 ml of water was added to the reaction mixture. After the concentration under reduced pressure, 40 ml of ethyl acetate was added thereto. The reaction mixture was washed with water (40 ml×1) and brine (40 ml×1). The organic layer was dried over sodium sulfate and concentrated under reduced pressure to obtain compound (53).

<Step 58>

Compound (53) was dissolved in methylene chloride. After nitrogen replacement, dimethylaminopyridine (500 mg, 4.03 mmol) and trifluoromethanesulfonyl chloride (500 μl, 4.68 mmol) were added to the reaction mixture, and they were stirred at 0° C. for 1 hour. 30 ml of ethyl acetate was added thereto and the mixture was washed with water (20 ml×2) and brine (20 ml×1). The organic layer was dried over sodium sulfate and then concentrated under reduced pressure to obtain compound (54).

<Step 59>

Compound (54) was dissolved in 80 ml of toluene. After nitrogen replacement, potassium phthalimide (1.40 g, 7.68 mmol) and 18-crown-6 (150 mg, 0.56 mmol) were added to the solution. The obtained mixture was stirred at 130° C. for 3 days. 100 ml of ethyl acetate was added thereto and the obtained mixture was washed with water (50 ml×2) and brine (50 ml×1). The organic layer was dried over sodium sulfate and then concentrated under reduced pressure. The reaction mixture was purified by the silica gel column chromatography with hexane/ethyl acetate=1/1 to obtain compound (55) (421 mg, 1.36 mmol, 60%).

<Step 60>

Compound (55) (389 mg, 1.25 mmol) was converted to compound (56) by a method described in a literature (Frieder W. Lichtenthaler, et al., Synthesis. 790, 1988).

<Step 61>

Compound (56) (309 mg, 1.21 mmol) was refluxed with 50 ml of 1 N hydrochloric acid for 12 hours. After cooling, white needle-like crystals thus formed were taken by the filtration. The filtrate was purified with Dowex 50W-X8 to obtain threonine (57) (50 mg, 0.400 mmol).

Synthesis of SAIL Serine:

[1,2,3-$^{13}C_3$; 2-$^{15}N$]serine was converted to an aldehyde (58) by a method described in a literature (Mark A. Blaskovich et al., J. Org. Chem., 63, 3631–3646, 1998). This product was asymmetrically reduced with (S)-BINAL-D according to scheme 11 and then hydrolyzed to convert it into SAIL serine (60). The structure of SAIL serine thus synthesized is shown in FIG. 1.

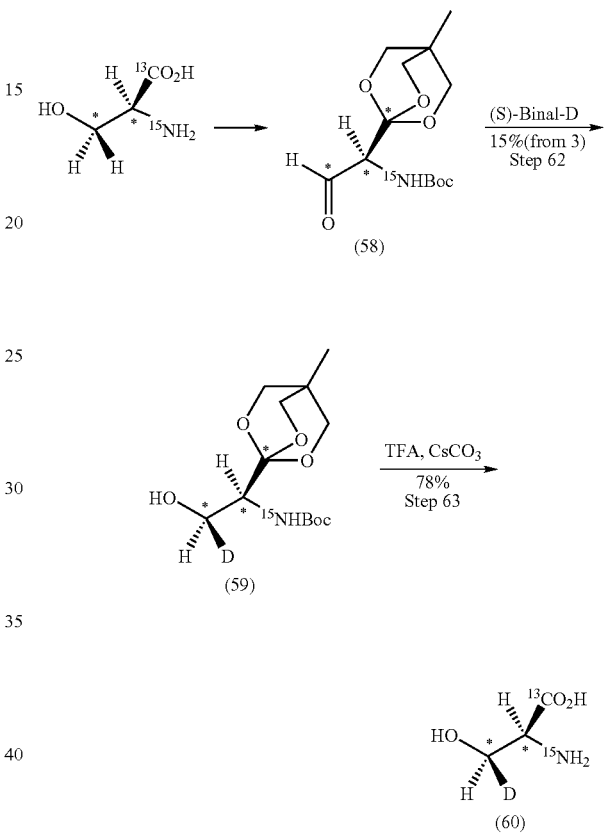

<Step 62>

LiAlD$_4$ (57.587 mol, 57.587 ml), EtOD (58.162 mmol, 2.738 g, 419 g) in THF (29 ml) and (S)-(−)-binaphthal (58.738 mmol, 16.819 g) dissolved in THF (80 ml) were successively fed into a reactor. After stirring the mixture at room temperature in argon stream for 30 minutes, the temperature was lowered to −100° C. A solution of compound (58) (3.728 g, 12.797 mmol) in THF (13 ml) was added to the reaction mixture and they were stirred for 3 hours and then at −78° C. for 18 hours. After the aftertreatment with 0.5 N HCl (200 ml) followed by filtration through Celite, the product was extracted with ether and then concentrated to obtain compound 59 (yield: 15%).

<Step 63>

Compound 59 (1.451 mmol) was dissolved in CH$_2$Cl$_2$ (30 ml). TFA (0.7 ml) and H$_2$O (0.50 ml) were added to the obtained solution, and they were stirred at room temperature for 30 minutes and then concentrated. CsCO$_3$ (9.6 mmol, 3.14 g) was added to the concentrate. The obtained mixture was dissolved in MeOH (22.5 ml) and H$_2$O (6 ml). After stirring for 17 hours, the product was acidified with HCl and then ion-exchanged to obtain SAIL-serine (60).

Synthesis of Cysteine:
SAIL cysteine was synthesized according to scheme 12.

Scheme 12

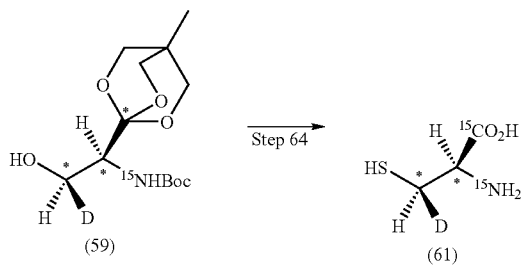

<Step 64>
Triphenylphosphine (2.46 mmol, 618 mg) was added to THF (6 ml), and the obtained mixture was cooled to 0° C. in argon atmosphere. 40% solution of DEAD in toluene (2.46 mmol, 1.12 ml) was added thereto. A solution of compound 59 (1.23 mmol, 356 mg) and thioacetic acid (2.46 mmol, 187 mg) in THF (3 ml) was added dropwise to the obtained mixture during 2 minutes. They were stirred at 0° C. for 1 hour and then at room temperature for 1 hour. After the concentration followed by the treatment with the column, compound 7 was obtained. THF (5.0 ml) and 2 N $NH_4OH$ (5 ml) were added to compound 7 and they were stirred at room temperature for 30 minutes and then concentrated to obtain compound 8. After removing the protecting group, the product was treated with an ion exchange resin to obtain intended compound 61 in a yield of 27%.

<Synthesis of Asparagine>
SAIL aspartic acid was synthesized by using $^{15}N$ labeled ammonia gas as the nitrogen source by a method described in a literature (A. F. Beecham, J. Am. Chem. Soc., 76, 4615, 1953).

Figure 11:
FIG. 11 shows a combination of stable isotope-labeled amino acids (SAIL amino acids) used for synthesizing calmodulin.

<Preparation of Labeled Protein>
As for the protein samples containing the above-described labeled amino acids, calmodulin protein was used as the model protein. Calmodulin was expressed by a method established by Zubay (Protein Expression, A Practical Approach, S. J. Higgins and B. D. Hames, pp. 201 to 223, Oxford University Press) selected from methods for cell-free protein synthesis. Differences between the method of the present invention and this known method are as follows: An E. coli extract was demineralized with PD-10 column (Amersham Biotech) and a mixture of the above-described amino acids in amounts proportional to the residue numbers was used (FIG. 11). pET-3a (Novagen) having calmodulin sequence inserted thereinto was used as the calmodulin expression DNA. After conducting the reaction in the cell-free synthetic system at 37° C. for 8 hours, 4.4 mg of purified calmodulin was obtained from 44 mg of the amino acid mixture. SAIL calmodulin thus prepared had a deuteration rate of 56%, and the number of signals in the side chains of amino acids was reduced to 60% based on that observed when they were not labeled with deuterium.

<NMR Determination of Labeled Protein>
For obtaining 1 mM of NMR sample from 4.4 mg of thus obtained SAIL calmodulin, this product was dissolved in a mixture of 100 mM KCl, 10 mM $CaCl_2$, 0.1 mM $NaN_3$ and 10% $D_2O$, having pH 6.5. For the comparison with SAIL calmodulin, deuterium-free calmodulin was used. For the NMR determination in all the cases, Bruker DRX600 or DRX800 was used at 37° C. XWINNMR ver. 2.6 (Bruker) or NMRPipe ver. 1.7 (Delaglio et al., J. Biomol. NMR, 6, 277–293, 1995) was used for NMR spectrum conversion. $^1H$-$^{13}C$ CT-HSQC spectra of them are shown in FIG. 12. In the spectrum of SAIL calmodulin, the sharpness of the signals and reduction in degeneracy are recognized. According to the sharpening of the line width of the spectrum of SAIL calmodulin, the sensitivity in the determination was several times higher than that of the uniformly labeled calmodulin.

Further, the following determination was conducted for the purpose of assigning NMR signals due to the main chain and side chains of calmodulin:
$^1H$-$^{15}N$ HSQC, HNCA, HN(CO)CA, HNCO, HN(CA)CO, HNCACB, CBCA(CO)NH, $^{15}N$-TOCSY, HBHA(CO)NH, HCCH-COSY, HCCH-TOCSY, TOCSY (aromatic) and NOESY (aromatic).

In the determination of them, deuterium decoupling by continuous waves was employed for $^1H$-$^{13}C$ CT-HSQC, HNCACB, CBCA(CO)NH, HBHA(CO)NH, HCCH-COSY and HCCH-TOCSY.

The spectra obtained by this determination were analyzed according to Sparky ver. 3. 105 (UCSF) to assign the signals.

For detecting NOE for the stereostructure calculation, $^{15}N$-NOESY, $^{13}C$-NOESY and $^1H^1H$ NOESY were determined.

<Calculation of Structure of Labeled Protein>
NOESY spectrum analysis and stereostructure calculation were conducted according to the assignment results of the main chain and side chain signals. In this method, a program CYANA (the Combined assignment and dynamics algorithm for NMR applications, c by Peter Guntert) (P. Guntert et al., J. Mol. Biol. 273, 283–298 (1997), T. Herrmann et al., J. Mol. Biol. 319, 209–227 (2002)) was used. This program was a combination of CANDID (NOESY automated analysis program) (Herrmann. T. et al., (2002). Protein NMR structure determination with automated NOE assignment using the new software CANDID and the torsion angle dynamics algorithm DYANA, J. MOL. Biol. 319, 209–227) and DYANA (torsion angle dynamics algorithm for structure calculation) (P. Guntert et al., (1997), Torsion angle dynamics for NMR structure calculation with the new program DYANA. J. Mol. Biol. 273, 283–298.). CYANA was operated on Linux cluster loaded with 14 Xeon processor. One cycle starts with NOE analysis and ends with the determination of 20 stereostructures. The cycle was repeated seven times by the automatic repetition. Data used for the final structure calculation after completion of the 7 cycles are shown in the following table:

| | |
|---|---|
| Chemical shift value | 1201 |
| Peak of $^{15}N$-edited NOESY | 1782 |
| Peak of $^{13}C$-edited NOESY | 1853 |
| Peak of 2D-NOESY | 159 |

Figure 13A:
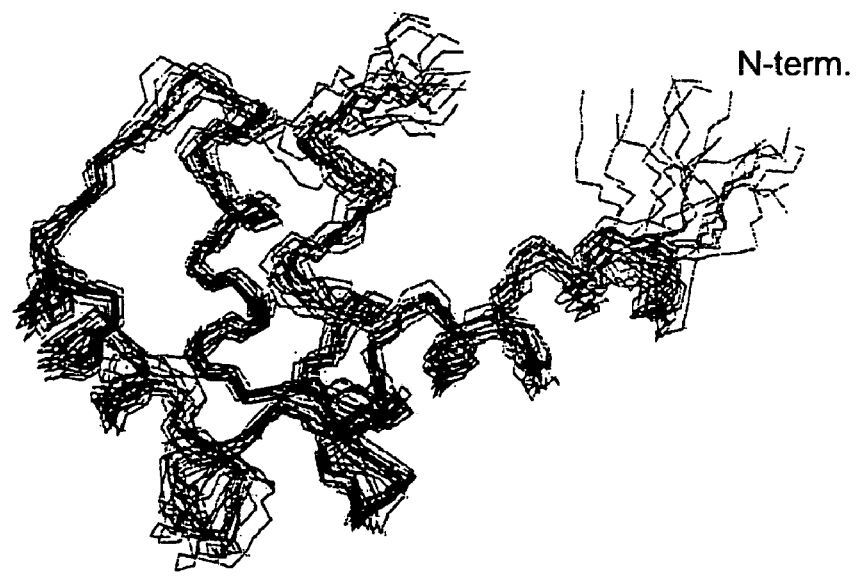
FIG. 13 shows the final 20 structures obtained by the structure calculation with CYANA of calmodulin protein synthesized from the combination of SAIL amino acids shown in FIG. 11.
Figure 13B:
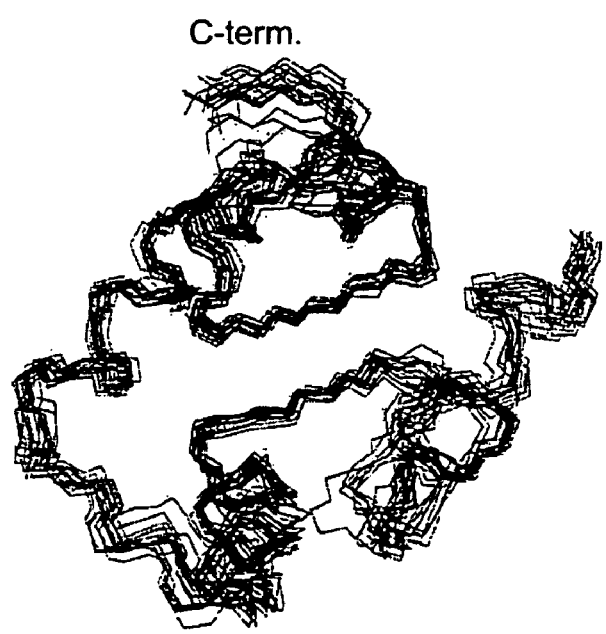

In the manual NOESY spectral analysis wherein the homogeneous, labeled sample was used, the calculation of the stereostructure took longer than several months. However, the structure can be determined in only 30 minutes by the above-described technique. This remarkable reduction in time is attained for the following reasons: Accurate signal analysis is made possible because signals unnecessary for the structure determination are removed and the sensitivity of the residual signals and the decomposition capacity are improved. Further, automated program is helpful. The final 20 structures thus obtained are shown in FIG. 13.

Namely, by the technique of the present invention, signals unnecessary for the structure determination are removed and the sensitivity of the residual signals is improved. Accordingly, it is made possible to rapidly and exactly analyze the signals of high-molecular protein and also to highly accurately determine the stereostructure thereof.

Thus, Examples 1 to 7 show the synthesis of amino acids having various isotope-labeled patterns and also the techniques of efficiently incorporating the labeled amino acids into a target protein by the cell-free protein preparation method without the metabolic transformation or dilution. Examples 1 to 7 also show the facts that precise structure information on high-molecular protein can be obtained by the determination of NMR spectrum of the obtained, labeled protein and that this information is far superior to that of conventional isotope NMR technique. In Example 7, RSD/SSD/SAD/PDM-amino acid-labeled protein was prepared by substituting all of 20 amino acid residues constituting protein with the labeled amino acids shown in FIG. 1 and this preparation was practically used for the stereo-structural determination. By the technique of the present invention in which the stereochemical assignment of residual protons is clear, it is made possible that the structure of the labeled protein solution can be rapidly and precisely determined. As shown in FIG. 10, by the technique of the invention of the present invention, the stereochemical assignment of remaining protons is made clear by the calculation experiments with a computer. This fact indicates that by this technique, the highly accurate determination of the solution structure of the labeled protein (c) is possible and that the obtained results are in no way inferior to those obtained when the information of all proton is obtained (b).

As a matter of course, various modes are possible in the details of the present invention.

Example 8

Synthesis of Stable Isotope-Labeled Fumaric Acid (1) Tert-Butyl Esterification of Stable Isotope-Labeled Acetic Acid An autoclave tube was cooled to −50° C. and liquefied isobutene (18 ml, 209 mmol) was poured into the tube. [1-$^{13}$C]acetic acid ($^{13}$CH$_3$$^{13}$CO$_2$H; a product of ISOTEC Inc.) (4 ml, 69.5 mmol) and Amberlyst (registered trade name) R15 (a product of Rohm Haas) (0.04 g, 1 wt. %) were added thereto, and the autoclave tube was tightly closed. The temperature was elevated to room temperature, and the reaction mixture was stirred for 5 hours. Amberlyst (registered trade mark) R15 was filtered out. The yield of obtained tert-butyl acetate was 91%.

(2) Conversion of Stable Isotope-Labeled Bromoacetic Acid into Tert-Butyl Ester Thereof An autoclave tube was cooled to −50° C. and liquefied isobutene (30 ml, 321 mmol) was poured into the tube. [1-$^{13}$C]bromoacetic acid ($^{13}$CH$_2$Br$^{13}$CO$_2$H; ISOTEC Inc.) (14.32 g, 103 mmol) and Amberlyst (registered trade mark) R15 (a product of Rohm Haas) (0.07 g, 0.5 wt. %) were added thereto, and the autoclave tube was tightly closed. The temperature was elevated to room temperature, and the reaction mixture was stirred for 24 hours. Amberlyst (registered trade name) R15 was filtered out. The yield of obtained tert-butyl bromoacetate was 97%.

(3) Synthesis of Stable Isotope-Labeled Fumaric Acid

Tert-butyl acetate (1.338 ml, 10 mmol) synthesized in above step (1), dimethylpropyleneurea (Aldrich Co.) (1.209 ml, 10 mmol) and 10 ml of tetrahydrofuran were fed into a three-necked flask and cooled to −78° C. in nitrogen atmosphere. Then 2 M lithium diisopropylamide/tetrahydrofuran solution (Aldrich Co.) (10 ml, 20 mmol) was added dropwise to the reaction mixture, and they were stirred at −78° C. for 1 hour. A solution of phenyl selenenyl chloride (Aldrich Co.) (1.928 g, 10 mmol) in 15 ml of tetrahydrofuran was added dropwise thereto.

After stirring at −78° C. for 2 hours, a solution of tert-butyl bromoacetate (1.477 ml, 10 mmol) synthesized in above step (2) in 10 ml of tetrahydrofuran was added dropwise to the reaction mixture. After stirring at −78° C. for 1 hour, the temperature was elevated to room temperature, and the reaction mixture was stirred at that temperature for 1 hour.

Saturated aqueous ammonium chloride solution was added to the reaction mixture to terminate the reaction. After the extraction with diethyl ether, the organic layer was dried over anhydrous magnesium sulfate and concentrated under reduced pressure.

The residue was dissolved in methylene chloride (40 ml). Sodium hydrogencarbonate (2.52 g, 30 mmol) was added to the obtained solution, and they were cooled to −78° C. m-Chloroperbenzoic acid (Tokyo Kasei) (3.451 g, 13 mmol) was added to the reaction mixture. The temperature was elevated to room temperature, and they were stirred for 1.5 hours. The obtained reaction mixture was washed with water, dried over anhydrous magnesium sulfate and concentrated under reduced pressure.

The residue was dissolved in 40 ml of tetrahydrofuran, and the obtained solution was cooled to 0° C. 30% aqueous hydrogen peroxide solution (5ml, 44 mmol) was added dropwise thereto. The temperature was elevated to room temperature, and they were stirred for 1 hour. After the extraction of the product from the reaction mixture with diethyl ether, the ether layer was successively washed with saturated aqueous sodium hydrogencarbonate solution, aqueous sodium dihydrogenphosphate solution and saturated aqueous sodium chloride solution. The ether layer was dried over magnesium sulfate and then concentrated under reduced pressure.

The residue was purified by the silica gel column chromatography with hexane/ethyl acetate=98/2 as the solvent to obtain di-tert-butyl fumarate. 20 ml of 1 M hydrochloric acid was added to obtained di-tert-butyl fumarate and they were stirred at 110° C. for 2 hours and then concentrated under reduced pressure to obtain stable isotope-labeled fumaric acid in a yield of 61% (0.713 g, 6.14 mmol).

Example 9

Conversion of Fumaric Acid into Diethyl D-Tartrate

Stable isotope-labeled fumaric acid (0.119 g, 1.027 mmol) obtained in Example 8 was dissolved in ethanol. The obtained solution was cooled to 0° C. and then 2.5 equivalents of thionyl chloride was added dropwise thereto. The temperature was elevated to room temperature and the obtained mixture was stirred for 2 hours.

The reaction mixture was concentrated to remove sulfur dioxide and then the residue was dissolved in diethyl ether. The obtained solution was washed with saturated aqueous sodium hydrogencarbonate solution and then dried over anhydrous magnesium sulfate. After the filtration by suction and the concentration, diethyl fumarate was obtained.

AD-mix-β (Aldrich Co.) (1.45 g) was dissolved in a solvent (10 ml) (tert-butanol/water=1/1). Methane sulfonamide (Aldrich Co.) (0.101 g, 1.061 mmol) was added to the obtained solution and then they were cooled to 0° C. Diethyl fumarate was added at once to the obtained mixture, and they were strongly stirred at 0° C. for 24 hours. Sodium sulfite (WAKO Co.) (1.5 g) was added to the reaction mixture, and they were stirred at room temperature for 1 hour. After the extraction with methylene chloride, the extract was washed with sodium dihydrogenphosphate.

After drying over anhydrous magnesium sulfate, the reaction mixture was concentrated under reduced pressure. The residue was purified by the silica gel column chromatography with hexane/ethyl acetate=7/3 to obtain diethyl D-tartrate (0.151 g, 0.732 mmol, 71%, >99% ee).

The results of the identification are shown in Table 1.

TABLE 1

[1, 2-$^{13}C_2$] Acetic acid tert-butyl ester
$^1$H[$^{13}$C] NMR(CDCl$_3$) δ 1.44(9H, s), 1.96(3H, s)
[1,2-$^{13}C_2$] Bromo acetic acid tert-butyl ester
$^1$H[$^{13}$C] NMR(CDCl$_3$) δ 1.47(9H, s), 3.74(3H, s)
[1,2,3,4-$^{13}C_2$] 2-Phenylselenenyl succinic acid di tert-butyl ester
$^1$H[$^{13}$C] NMR(CDCl$_3$) δ 1.38(9H, s), 1.42(3H, s), 2.63(1H, dd, J=5.4Hz, 16.7Hz), 2.83(1H, dd, J=10.0Hz, 17.0Hz), 3.84(1H, dd, J=5.6Hz, 9.9Hz), 7.16–7.34(3H, m), 7.56–7.64(2H, m)
$^{13}$C NMR(CDCl$_3$) δ 29, 38, 135, 171
[1,2,3,4-$^{13}C_2$] Fumaric acid di tert-butyl ester
$^1$H[$^{13}$C] NMR(CDCl$_3$) δ 1.48(18H, s), 6.66(2H, s)
[1,2,3,4-$^{13}C_2$] Fumaric acid di ethyl ester
$^1$H[$^{13}$C] NMR(CDCl$_3$) δ 1.32(6H, t, J=7.2Hz), 4.26(4H, q, J=7.2Hz, 14.1Hz), 6.84(2H, s)
$^{13}$C NMR(CDCl3) δ 134, 165
[1,2,3,4-$^{13}C_2$] Tartaric acid di ethyl ester
$^1$H[$^{13}$C] NMR(CDCl$_3$) δ 1.30(6H, t, J=7.2Hz), 3.25(2H, h), 4.29 (4H, q, J=7.3Hz, 14.3Hz), 4.51(2H, s)
$^{13}$C NMR(CDCl3) δ 72, 172

In the determination, 1HNMR was $^{13}$C decoupled ($^1$H [$^{13}$C]NMR) with Valian INOVA 300, and the data were compared with those of non-labeled sample to obtain the results.

As described above in detail, by the first to the third modes of the present invention, the deuteration in the whole protein and the improvement in the sensitivity of the remaining signals are made possible. Thus, rapid, accurate signal analysis of high-molecular protein and highly precise stereostructure determination thereof are made possible over the range of the conventional techniques.

Namely, the following effects are obtained by the present invention:

(1) The line width of NMR signal is remarkably sharpened (improvement in the signal solving power).
(2) The determination sensitivity is improved (shortening of the determination time)
(3) The accuracy of NMR spectral analysis is improved, and shortening of the analysis time and automation of the analysis are made possible.
(4) The scope of the molecular weight of protein to which NMR is applicable is widened (at least 2 times wider; the determination of the structure of protein having a molecular weight of about 50,000 is made possible).
(5) The accuracy in the structure analysis is improved (because of the automatic stereospecific assignment of all the signals).
(6) The structure determination and structure information are possible according to the signals of even the end of a side chain (possibility of the application of the technique to genome drug development and drug design).

As described above, the present invention and the technique of determining the structure clearly assumed as an extension of the invention are very effective in determining the structure with a high accuracy at a high throughput.

In addition, modes 4 to 7 in the present invention provide the method for efficiently producing regio-selectively stable isotope-labeled fumaric acid and tartaric acid, which could not be easily obtained in the prior art, by coupling stable isotope-labeled acetic acid and stable isotope-labeled bromoacetic acid which are inexpensive stable isotope reagents. According to this method, isotope-labeled fumaric acid and tartaric acid of any desired pattern can be produced, and the yield and optical purity of the products are high.

Recently, stable isotope-labeled fumaric acid and stable isotope-labeled tartaric acid are used in, for example, the analysis of the stereostructure of protein and the demand thereof is increasing. Under these circumstances, the method of the present invention for producing the regio-selectively stable isotope-labeled fumaric acid and tartaric acid can be considered to be highly utilizable.

What is claimed is:

1. A combination of stable isotope-labeled amino acids constituting a target protein, wherein all amino acids constituting the target protein have the following label patterns:
   (a) when a methylene group having two hydrogen atoms is present, one methylene hydrogen atom is deuterated,
   (b) when prochiral gem-methyl groups are present, all hydrogen atoms in one methyl group are completely deuterated and hydrogen atoms in the other methyl group are partially deuterated,
   (c) when a methyl group other than those stated above in (b) is present, then all hydrogen atoms except one of them in the methyl group are deuterated or all hydrogen atoms in the methyl group are deuterated,
   (d) when the aromatic ring has hydrogen atoms, the hydrogen atoms in the aromatic ring may be partially deuterated,
   (e) after the deuteration in above (a), (b), and (c), all carbon atoms of hydrogen atom-containing methylene group and/or methyl group are replaced with $^{13}$C, and
   (f) all nitrogen atoms are replaced with $^{15}$N.

2. The combination of stable isotope-labeled amino acids of claim 1, wherein when said pattern is (d), then when the aromatic ring has hydrogen atoms, the hydrogen atoms in the aromatic ring are partially deuterated.

3. The combination of stable isotope-labeled amino acids of claim 2, wherein (e) all carbon atoms of hydrogen atom-containing methylene group and methyl group are replaced with $^{13}$C after the deuteration in (a), (b) and (c).

4. The combination of stable isotope-labeled amino acids of claim 3, wherein carbon atoms constituting carbonyl group and guanidyl group in the amino acids are replaced with $^{13}$C.

5. A method for producing a target protein composed of stable isotope-labeled amino acids, which comprises synthesizing a cell-free protein by using the combination of the stable isotope-labeled amino acids set forth in claim 1.

6. The method for producing a target protein according to claim 5 wherein a combination of stable isotope-labeled amino acids of claim 2 is used as the all amino acids constituting the target protein.

7. The method for producing a target protein according to claim 5 wherein a combination of stable isotope-labeled amino acids of claim 3 is used as the all amino acids constituting the target protein.

8. The method for producing a target protein according to claim 5 wherein a combination of stable isotope-labeled amino acids of claim 4 is used as the all amino acids constituting the target protein.

9. A method for analyzing the structure of a target protein using NMR, which comprises analyzing the structure of the target protein, in which all the amino acids constituting the target protein are replaced with the stable isotope-labeled amino acids of claim 1, by NMR spectral determination.

10. The method for analyzing the structure of a target protein using NMR according to claim 9 wherein all the amino acids constituting the target protein are replaced with the stable isotope-labeled amino acids of claim 2.

11. The method for analyzing the structure of a target protein using NMR according to claim 9 wherein all the amino acids constituting the target protein are replaced with the stable isotope-labeled amino acids of claim 3.

12. The method for analyzing the structure of a target protein using NMR according to claim 9 wherein all the amino acids constituting the target protein are replaced with the stable isotope-labeled amino acids of claim 4.

13. A method for producing regio-selectively stable isotope-labeled fumaric acid, which comprises coupling stable isotope-labeled acetic acid with stable isotope-labeled bromoacetic acid.

14. A method for producing regio-selectively stable isotope-labeled fumaric acid, which comprises the steps of:
   tert-butyl-esterifying stable isotope-labeled acetic acid and stable isotope-labeled bromoacetic acid;
   oxidatively coupling said tert-butyl-esterified acids to form a product; and
   hydrolyzing the product with an acid.

15. The method according to claim 14, wherein said tert-butyl-esterifying step comprises bringing stable isotope-labeled acetic acid and stable isotope-labeled bromoacetic acid into contact with liquefied isobutene in the presence of an acid catalyst to convert the stable isotope-labeled acetic acid and stable isotope-labeled bromoacetic acid into tert-butyl esters thereof.

16. A method for producing regio-selectively stable isotope-labeled fumaric acid, comprising the steps of:
   converting tert-butyl acetate obtained from stable isotope-labeled acetic acid into an enolate thereof to form a stable isotope-labeled bromoacetic acid;
   adding tert-butyl bromoacetate obtained from said stable isotope-labeled bromoacetic acid in the presence of an organoselenium compound;
   oxidizing a compound obtained from said adding step; and
   hydrolyzing a product obtained in said oxidizing step.

17. A method for producing stable isotope-labeled tartaric acid, which comprises oxidizing the stable isotope-labeled fumaric acid produced by the method of claim 13 with an asymmetric dihydroxylating agent and hydrolyzing the obtained product.

18. The method for producing stable isotope-labeled tartaric acid according to claim 17, wherein the asymmetric dihydroxylating agent is selected from the group consisting of AD-mix-α and AD-mix-β.

19. A group of amino acids constituting a protein, wherein all of said amino acids constituting the protein have one or more deuterium atoms in a predetermined labeling pattern selected from the group consisting of:
   (a) at least one hydrogen atom is a deuterium atom, provided that at least one hydrogen atom in one or more methylene groups is not a deuterium atom,
   (b) when prochiral gem-methyl groups are present, each hydrogen atom in one prochiral gem-methyl group is a deuterium atom,
   (c) when prochiral gem-methyl groups are present, hydrogen atoms in at least one prochiral gem-methyl group are partially replaced with deuterium atoms,
   (d) one hydrogen atoms in a methylene group is a deuterium atom while, when an aromatic ring has hydrogen atoms, the hydrogen atoms in the aromatic ring are partially replaced with deuterium atoms, and
   (e) when a methyl group other than a prochiral gem-methyl group is present, then all hydrogen atoms except one of them in the methyl group are replaced with deuterium atoms or all hydrogen atoms in the methyl group are replaced with deuterium atoms; and
   wherein all nitrogen atoms of said group of amino acids are replaced with $^{15}$N.

20. The group of amino acids according to claim 19, wherein all carbon atoms having remaining hydrogen atoms, which have not been replaced with deuterium atoms, in at least one of said methylene group, said prochiral gem-methyl group and said methyl group, are replaced with $^{13}$C.

21. A method for analyzing the structure of a target protein, comprising:
   detecting an NMR spectrum of said target protein, in which all of the amino acids constituting the target protein are replaced with the group of amino acids according to claim 19; and
   analyzing the structure of the target protein based on the detected NMR spectrum.

* * * * *

UNITED STATES PATENT AND TRADEMARK OFFICE
CERTIFICATE OF CORRECTION

| | | |
|---|---|---|
| PATENT NO. | : 7,022,310 B2 | Page 1 of 1 |
| APPLICATION NO. | : 10/872163 | |
| DATED | : April 4, 2006 | |
| INVENTOR(S) | : Kainosho et al. | |

It is certified that error appears in the above-identified patent and that said Letters Patent is hereby corrected as shown below:

At column 1, line 12, "Application No. 2002-22447 filed on…" should read "…Application No. 2002-22446 filed on…".

At column 15, line 59, "protons are is omitted" should read "…protons are omitted.".

Signed and Sealed this

First Day of August, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,022,310 B2 | Page 1 of 1 |
| APPLICATION NO. | : 10/872163 | |
| DATED | : April 4, 2006 | |
| INVENTOR(S) | : Kainosho et al. | |

It is certified that error appears in the above-identified patent and that said Letters Patent is hereby corrected as shown below:

At column 14, line 65, "Th filtrate was purified" should read "The filtrate was purified…".

Signed and Sealed this

Thirty-first Day of October, 2006

JON W. DUDAS
*Director of the United States Patent and Trademark Office*